United States Patent [19]

Cotton et al.

[11] Patent Number: 5,217,863
[45] Date of Patent: Jun. 8, 1993

[54] DETECTION OF MUTATIONS IN NUCLEIC ACIDS

[75] Inventors: Richard G. H. Cotton, Canterbury, Australia; Robert D. Campbell, Headington, Great Britain

[73] Assignee: Medical Research Council, London, England

[21] Appl. No.: 814,061

[22] Filed: Dec. 26, 1991

Related U.S. Application Data

[63] Continuation of Ser. No. 306,153, Feb. 6, 1989, abandoned.

[30] Foreign Application Priority Data

Feb. 4, 1988 [GB] United Kingdom ............... 8802508

[51] Int. Cl.$^5$ .................. C12Q 1/68; C07H 15/12; C07H 17/00; C12N 15/00
[52] U.S. Cl. ........................... 435/6; 536/23.1; 536/23.2; 536/24.3; 536/24.31; 935/77; 935/78
[58] Field of Search ............... 435/6; 536/27; 935/77, 935/78

[56] References Cited

U.S. PATENT DOCUMENTS 4,794,075 12/1988 Ford et al. ..................... 435/6

FOREIGN PATENT DOCUMENTS 2179735 3/1987 United Kingdom .

OTHER PUBLICATIONS

Kochetkov et al., (1972) Organic Chemistry of Nucleic Acids, part B. Plenum, London and New York.
Morozova et al., (1964) Biokhimiya 29, 17.
Rubin et al., (1980) Nucl. Acid Res. 8 pp. 4613-4619.
Maniatis et al., Molecular Cloning-A Laboratory Manual (1982), cold Spring Harbor Laboratory, pp. 475-478.
Friedman et al., Nucleic Acids Research, vol. 5, No. 2, Feb. 1978, pp. 615-622.
Glikin et al., Nucleic Acids Res., vol. 12, No. 3, 1984, pp. 1725-1735.
Cotton et al., Proceedings National Academy of Sciences, USA, vol. 85, Jun. 1988, pp. 4397-4401.
Johnston et al., Biological Abstracts, Abstract No. 33128, vol. 81, 1986.
Lilley et al., Chemical Abstracts, Abstract No. 33961w, vol. 101, 1984, p. 125.
Cashmore et al., Chemical Abstracts, Abstract No. 84180t, vol. 75, 1971, p. 12.

Primary Examiner—Amelia Burgess Yarbrough
Assistant Examiner—Mindy B. Fleisher
Attorney, Agent, or Firm—Oblon, Spivak, McClelland, Maier & Neustadt

[57] ABSTRACT

A method of detecting point mutation in nucleic acids is described which comprises hybridizing a piece of control DNA or RNA without mutations with a piece of test DNA or RNA generally corresponding to the test DNA or RNA but possibly with mutations to produce a heteroduplex, treating the heteroduplex with hydroxylamine or osmium tetroxide and with piperidine, and subjecting the resulting material to separation treatment. Individual strands of both senses of control nucleic acid can be labelled in turn allowing detection of all possible mutations.

15 Claims, 14 Drawing Sheets

```
          1  NcoI
218 (+) 5' ATGGCCATGGACCTTGGTGAATTGTGTGAAGACACAATCACGTACAAGTGTCCCCTTCTCAGGCAGAATGAGCCAGAGACATAGACTGC
    (-) 3' TACCGGTACCTGGAACCACTTAACACACTTCTGTGTTAGTGCATGTTCACNGGGAGTCCGTCTTACTCGGTCTTCTGTATCTGACG
                                                                                        ••*72    • •
NGC (+) 5' ................................................T.................A............T..T

91                                                       M
218 (+) TGGTGCAACTCCACGTCCACGTGGGTAACCTATGGGACTTGTACCACCACGGGGAACATAGAAGAGAAAAAGATCAGTGGCACTCGTT
    (-) ACCACGTTGAGGTGCAGGTGCACCATTGGATACCCTGAACATGGTGGTGCCCTCTGTATCTTCTCTTTTTTCTAGTCACCGTGAGCAA
                                    *111    •                   *141   • •
NGC (+) ............T.......A.......G.....................A..........C......

181
218 (+) CCACATGTGGGAATGGACTGGAGACGGAACTGAAACATGGATGTCATCAGAAGGGGCTTGAAACATGCCAGAGAATTGAAATTTGG
    (-) GGTGTACACCCTTACCCTGACCTCTGCCGTTGACTTTGTACCTACAGTAGTCTTCCCCGAACCTTTGTACGGGTCTCTTAACTTTAAACC
                                      *207
NGC (+) ..................A.........................C..............

271
218 (+) ATCCTGAGACATCCAGGCTTCACCATAATGGCAGCAATCCTGGCATACACCATAGGGACGACACATTCCAGAGACACTGATTTTCATC
    (-) TAGGACTCTGTAGGTCCGAAGTGGTATTACCGTCGTTAGGACCGTATGTGGTATCCCTGCTGTGTAAAGGTCTCTGCTGACTAAAAGTAG
                                                           *327       ••*342  +348
NGC (+) ...T....................................................A.................C......

361                             E
218 (+) TTACTGACAGCTGTCGCTCCTTCAATGACAATGCGTTGCATAGGAATATCAAATAGAGACTTTGTAGAAGGGGTTTCAGGAGGAGCTGG
    (-) AATGACTGTCGACAGCGAGGAAGTTACTGTTACGCAACGTATCCTTATAGTTTATCTCTGAAACATCTTCCCAAAGTCCTCCTTCGACC

NGC (+) ..........

HindII
        451
218 (+) GTTGAC
    (-) CAACTG

NGC (+) ......
```

Fig.6

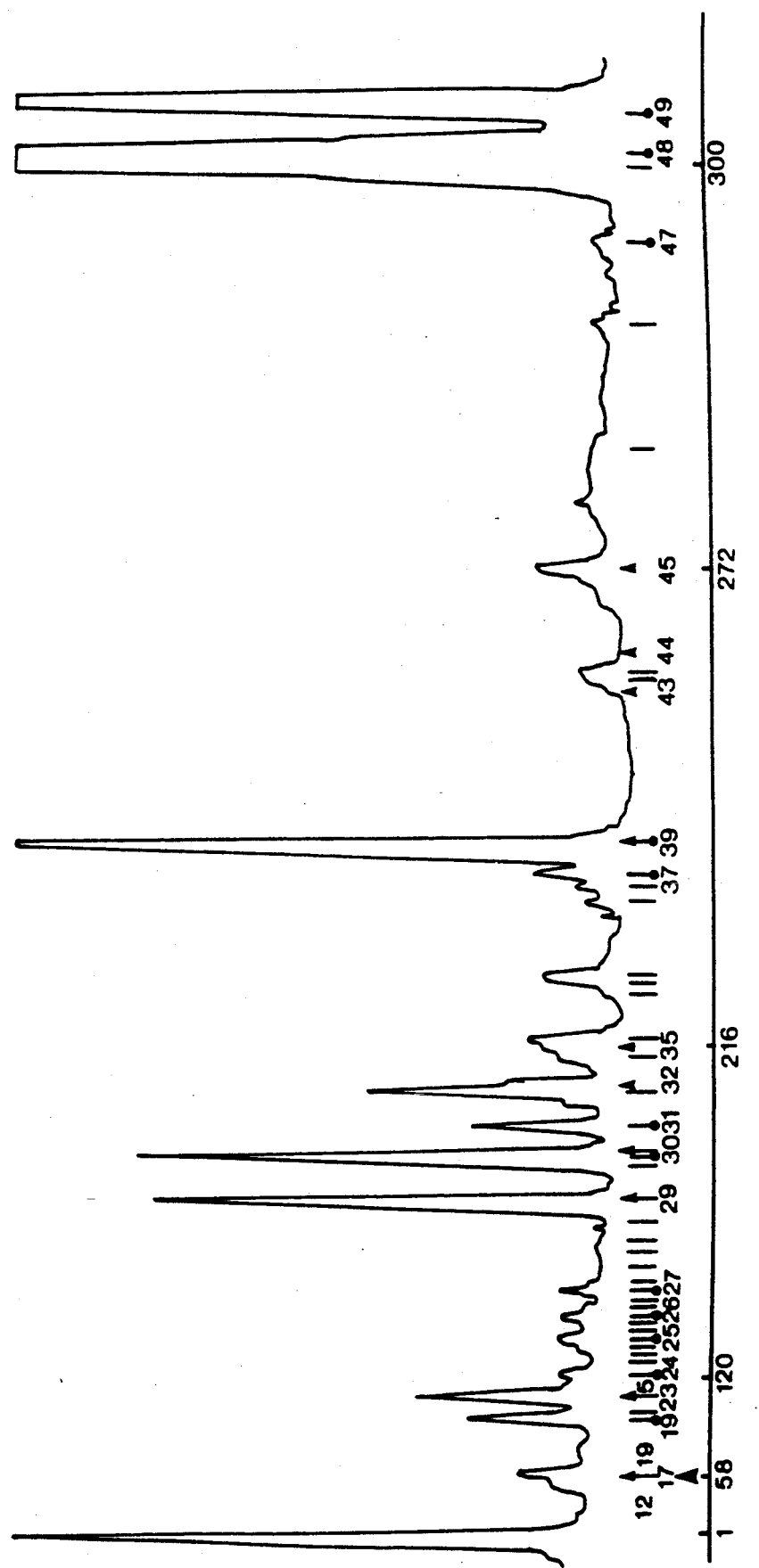

DETECTION OF MUTATIONS IN NUCLEIC ACIDS

This application is a continuation of application Ser. No. 07/306,153, filed on Feb. 6, 1989, now abandoned.

FIELD OF INVENTION

This invention concerns the detection of mutations in nucleic acids. The method described herein can be used to detect mutations in all types of naturally occurring nucleic acid, such as human, animal, plant, viral and microbial nucleic acids.

BACKGROUND TO THE INVENTION

Nucleic acids DNA and RNA consist of a sugar-/phosphate backbone with attached linear sequence of bases: thymine (T), cytosine (C , guanine (G) and adenine (A) in the case of DNA and C,G,A and uracil (U) in the case of RNA. The bases bind to one another as follows:

C-G

A-T/U

The sequence of bases determines the sequence of amino acids of protein produced from the nucleic acids, and mutations in nucleic acids result in variations in the sequences of bases and thereby amino acid sequence.

The definition of exact single base changes in genes as a result of mutation is an important goal in the study of genetics. As the sequencing of complete genes in search of base changes is tedious several attempts have been made to make the search more efficient (see references 1, 2, 3, 4,5). Heteroduplexes were formed between wild type and variant DNA and it was found that single strand specific SI nuclease could cleave the DNA at the point of the mismatched bases in the DNA (1). The differential mobility of native and denatured DNA/DNA heteroduplexes coupled with their differential melting temperatures has been exploited by Myers et al (2). Since this method was not generally applicable (reviewed in 3), Myers et al (3) described a method where mismatches in heteroduplexes between RNA and DNA were cleaved by ribonuclease A. An alternative approach where RNase A is used to cleave mismatches in RNA/RNA heteroduplexes has also been described (4). Finally Novak et al (5) have reported that single base pair mismatches in DNA/DNA heteroduplexes are reactive with, but are not cleaved by, a carbodiimide.

The known methods either do not detect and localise all mutations, or have not been shown to do so, and the present invention aims to provide an improved method, which in preferred embodiments at least, is capable of detecting all mutations.

SUMMARY OF THE INVENTION

According to one aspect of the present invention there is provided a method of detecting a point mutation in a nucleic acid, comprising hybridizing a piece of control DNA or RNA without mutations with a piece of test DNA or RNA generally corresponding to the test DNA or RNA but possibly with mutations to produce a heteroduplex, treating the heteroduplex with hydroxylamine or osmium tetroxide and with piperidine, and subjecting the resulting material to separation treatment.

Any point mutations in the test DNA or RNA (either substitution, addition or deletion of a base or bases) will result in a base pair mismatch, with unbound base or bases. It has been found that hydroxylamine reacts with mismatched C and osmium tetroxide reacts with mismatched T (and to a lesser extent mismatched C), resulting in cleavage at the point of mismatch on addition of piperidine. If cleavage has occurred at one or more sites this will be apparent from the result of separation treatment, the number of fragments indicating the number of cleavages and hence the number of mutations of the type under consideration.

It has also been found that matched T or C bases which are one or two bases (or sometimes more) from a given mismatched A or G base, often react with hydroxylamine and osmium tetroxide, thus making the indirect detection of mismatched A and G bases possible. Similarly nearby matched T and C bases become reactive when next to or nearby insertions and deletions, making detection of these possible also.

By use of labelled (either end labelled or internally labelled) DNA or RNA as appropriate, information can be obtained about the location of mutations. Any convenient label may be used, including, e.g., radioactive labels, fluorescent labels, and enzyme labels in a manner well known to those skilled in the art. When only one of the two strands in a heteroduplex is labelled mutations may be detected indirectly, as matched bases near or next to mutations in a situation where the mutation does not lead to a mismatched T or C in the labelled strand.

Separation is conveniently by electrophoresis, but other techniques can also be used.

The hydroxylamine is conveniently in the form of a salt, e.g. hydroxylamine hydrochloride, or a derivative, e.g. O-methyl hydroxylamine, but other forms may also be used.

Hydroxylamine treatment is preferably carried out by incubation with 2M hydroxylamine hydrochloride for 2 hours at 37° C. at pH6. Osmium tetroxide treatment is preferably carried out by incubation with 2.4% w/v osmium tetroxide for periods of up to 1 hour at 37° C. in a buffer of pH 7.7.

Due to the nature of the chemicals and concentrations used, hydroxylamine and osmium tetroxide treatments are preferably carried out on separate samples.

Mismatched A and G are not detected by use of hydroxylamine or osmium tetroxide, but such mutations can be detected by use of a complementary strand of test nucleic acid and a complementary probe.

For full mutation information on a particular piece of test DNA, four reactions are therefore required:
 a) test piece treated with osmium tetroxide
 b) test piece treated with hydroxylamine
 c piece complementary to test piece treated with osmium tetroxide
 d) piece complementary to test piece treated with hydroxylamine.

Thus in a preferred aspect the invention provides a method of detecting all point mutations in a nucleic acid wherein a piece of control DNA or RNA is hybridized with a piece of test DNA or RNA generally corresponding to the control DNA or RNA but possibly with mutations to produce a heteroduplex, characterised in that in separate heteroduplexes each of the strands of the control are labelled in turn in separate samples and that each of these samples is divided in two, one portion being treated with osmium tetroxide and the other with hydroxylamine and all four sample portions are treated with piperidine and the resulting material subjected to separation treatment.

Useful information may nevertheless be obtainable from less complete testing, e.g. by addition of osmium tetroxide only to test material, locating any T (and possibly also C) mismatches. This limited information may be sufficient to be of use, e.g. if it is merely required to know whether a piece of DNA has mutations or not, in preliminary screening, or to obtain a pattern of difference.

Use of an end labelled probe in conjunction with partial cleavage enables generation of a pattern of difference between two nucleic acids in the form of a "fingerprint" by detecting multiple differences in one experiment.

Mutations in RNA can also be detected. Only limited information can be obtained by testing single stranded (SS) test RNA (e.g. mRNA or SS RNA viruses) with control RNA or DNA. However, full information can be obtained by producing cDNA from the SS RNA of interest and testing this DNA with control DNA.

The method can be used to examine DNA which is available in larger quantities such as cloned DNA, viruses and also possibly to RNA isolated from cells, and it is believed the method is also applicable to genomic DNA.

Potential specific applications include the following:

(a) Inherited Disease

This is the most obvious potential application but perhaps not the one which may attract the most use. When the method has been shown applicable to genomic DNA it would be possible to have oligonucleotides available for particular mutations such as the sickle mutation such that in the disease state a mismatched T or C is present in the probe which can be cleaved by osmium tetroxide or hydroxylamine, respectively. The method should also be applicable to mRNA and there are situations where it may be of diagnostic use.

The method should be compatible with the dot blot and bead methods worked out in London for sickle cell disease by Drs. Williamson and Malcolm.

(b) Comparison of Related Virus Isolates

Viruses can change their sequence rapidly in a short time and typical examples are Influenza and Human Immunodeficiency viruses. The usual method of comparison of these variant strains with a standard is sequencing and then comparison of sequences. Sequencing is tedious and subject to error, and the current method is capable of giving a fingerprint of the difference of one virus from another.

(c) Oncogenes

Many oncogenes have been characterised which differ from normal by a singe base. Comparisons have been made by sequencing as for viruses. The method of the invention should allow a rapid decision as to whether one oncogene has a base change relative to another.

(d) Check of in Vitro Mutagenesis

Many scientists are carrying out experiments to alter specific bases in a gene to see what effect this has on function. Once this has been done there is a need to check (a) that the required base change has actually been effected, and (b) that other unwanted base changes have not been created. This is currently done by sequencing and sequence comparison and would be much more conveniently done by the method of the invention.

The invention will be further described by way of reference to the following examples. Example 1 concerns work on the 21-hydroxylase gene. This gene was chosen both because of its medical importance and because of the large amount of polymorphism in the gene and pseudogene (see reference 6). Example 2 concerns work on DNA/RNA heteroduplexes of nucleic acids derived from different strains of dengue virus type 2. Example 3 concerns further work on the 21-hydroxylase gene.

BRIEF DESCRIPTION OF THE DRAWINGS

Reference is also made to the accompanying drawings, in which:

FIG. 6 is a comparison of sequences of cDNA for the New Guinea C (NGC) and PUO-218 strains of dengue virus type 2;

FIGS. 11A, 11B, 11C, and 11D show densitometer tracings of tracks of analyses shown in FIG. 10.

EXAMPLE 1

Figure 1:
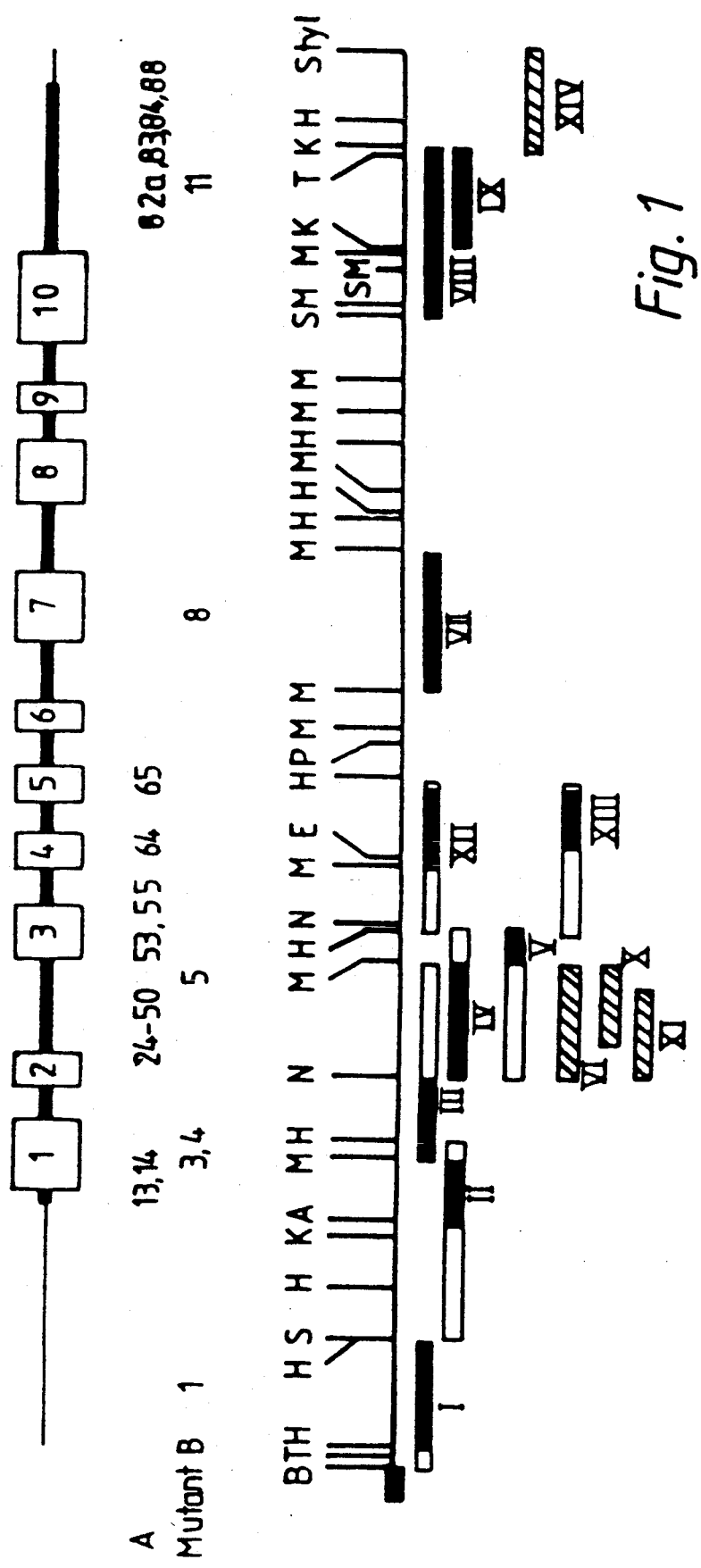
FIG. 1 is a map of the wild type 21 hydroxylase B gene, with the upper line showing the exon/intron structure of the gene and the lower line being a restriction map showing the restriction sites used for generating fragments for subcloning into M13.

Work was carried out using the wild type 21-hydroxylase B gene, as illustrated in FIG. 1. In the Figure, restriction enzymes whose sites are shown are as follows: A, AccI; B, Bam HI; E. EcoRI; H, Hinf I; K, Kpn I; M, MspI; N, Nco I; P, Pvu II; Ps, PstI; S, SstI; Sa, Sau 3AI; Sm, Sma I; St, Sty I, T, Taq I. The numbers above the restriction map show the approximate positions of differences of the mutant B gene (6) (lower) and the A gene (upper) from the wild type B gene with the numbering starting from the first difference from the 5' end. Only some of those differences studied are shown. The horizontal bars represent B, mutant B or A gene DNA from M13 subclones used as specified in Table 1 or from pAT plasmid DNA used for end labelling studies (Table 1). The shaded portion of these bars represent that portion of the DNA used as probes. The hatched boxes represent the pAT plasmid DNA used for the end labelling studies. The Roman numerals represent the regions used to produce probes and are referred to in Table 1.

In Table 1 the symbols have the following meanings:

*: C mismatches were studied with hydroxylamine (and some with osmium tetroxide (see $)) and T mismatches with osmium tetroxide. The first of the two mismatched bases is that in the labelled strand.

+: The entry gives the probe sense, area of the gene used and the gene used (see FIG. 1). B is the wild type gene, M the mutant B gene and A the A pseudogene.

$: The cleavage is defined in Methods below. +ve indicates cleavage seen but not quantitated. E denotes that end labelled probe was used and cleavage seen but not quantitated. (R) indicates position of cleavage is defined by sequencing ladders run in parallel. Values in brackets refer to cleavage of C mismatches with osmium tetroxide.

**: Mismatched bases which are cleaved are bracketed and nearby mismatched bases are underlined. Left hand end is 5'.

++: Mutations were described after publication (6).

MATERIALS AND METHODS

Preparation of DNA and Probes

Plasmid and M13 subclone DNA were prepared by standard methods (6). Internally labelled DNA probes were prepared from M13mp8 or M13mp9 subclones containing the DNA fragments which were used to generate the sequence of the 21-OHase A gene, the 21-OHase B gene and the mutant 21-OHase B gene (6).

Subclones carrying the desired DNA fragment in the sense opposite to the sense of the probe required were labelled by standard methods (9) using the M13 universal sequencing primer. All nucleotides were at 0.25 mM except dATP which was only added to a level such that the alpha-$^{32}$P-dATP was diluted 1:9. Typically 2 ng of primer was annealed with 50 ng of M13 DNA in 6.5 ul at room temperature for 30 min after initial heating at 90° C. for 4 min. Nucleotides were then added together with 1 ul alpha-$^{32}$P-dATP (3000 Ci/mmol, The Radiochemical Centre, Amersham, UK) and 1 ul (7.5 U) Klenow (Pharmacia) in a final volume of 17.6 ul. Incubation was at room temperature (20°-24° C.) for 1 hr. All nucleotides were then added at 0.25 mM to chase for a further 30 min. Samples were then extracted with chloroform/phenol, and the DNA was ethanol precipitated. Immediately after labelling DNA was digested (in a final volume of 20-50 ul) with restriction enzymes appropriate for the particular heteroduplex being studied (see Table 1) using the suppliers specifications.

End-labelled DNA probes (see Table 1) were derived from the appropriate digests of the 3.7 kb Taq I fragment of the wild type or mutant 21-OHase B genes, or the 5.5 kb Bgl II/BamHI fragment of the 21-OHase A gene, cloned in the Pvu II site of the plasmid pAT153/-PvuII/8 (6). Fragments were purified by electrophoresis in 4% native polyacrylamide gels.

Heteroduplex Formation

Heteroduplexes contained unlabelled DNA derived from digests of the plasmid subclones with restriction enzymes appropriate for the particular heteroduplex being studied (see Table 1). Purified labelled probe and digested plasmid DNA were mixed in an appropriate ratio. This ranged from a 12-fold molar excess of unlabelled to labelled DNA for end-labelled probes, to 50 or 200 fold molar excess for internally labelled probes. The mixture (20-100 ul) was heated at 100° C. for 5 min and annealed at 42° C. for 1 hr in 0.3 M NaCl/3.5 mM $MgCl_2$/3mM Tris pH 7.7. Heteroduplex DNA was precipitated with ethanol then taken up in distilled water so as to be 1000 cpm/ul and up to 6000 cpm were used per tube.

Hydroxylamine Treatment of DNA 1.39 gm hydroxylamine (Analar, BDH, Poole) was dissolved in 1.6 ml of distilled water and the pH was adjusted to 6.0 with diethylamine (Fluka). The final volume was about 4 ml giving a concentration of hydroxylamine of about 2.5M.

DNA in 6 ul distilled water was treated with 20 ul hydroxylamine solution at 37° C. for 2 hrs. Times other than this are indicated in the time course experiments. The reaction was stopped by transfer to ice and addition of 100 ul stop solution containing 0.3M sodium acetate/0.1 mM $Na_2$ EDTA, pH 5.2 and 25ug/ml tRNA (baker's yeast, Boehringer), and the DNA was precipitated with ethanol. After a further ethanol precipitation the DNA pellet was washed once with 70% ethanol and dried.

Osmium Tetroxide Treatment of DNA

DNA in 6 ul distilled water was treated with 15 ul of 2.4% (w/v in water) osmium tetroxide solution (Aldrich) in a total volume of 24.5 ul with 1 mM-EDTA/10 mM Tris pH 7.7 and 1.5% pyridine. Incubation was at 37° C. for times up to 1 hr as indicated in the text. The reaction was stopped as described for hydroxylamine.

Piperidine Cleavage

Chemical cleavage of the C and T nucleotides which had reacted with hydroxylamine and/or osmium tetroxide was achieved by incubation of the heteroduplexes with piperidine (8). 50 ul 1M piperidine was added to each tube containing the dry DNA pellet and incubated at 90° C. for 30 min. DNA was precipitated with ethanol, washed with 70% ethanol and dried. In the case of osmium tetroxide treated DNA, ethanol precipitation after piperidine treatment was in a dry ice/methanol bath and all operations after this were at or below 4° C. until the dried pellet was obtained.

Electrophoresis of Products

Samples were incubated in 10 ul formamide dyes at 100° C. for 4 min before application to 4% denaturing urea gels (8). Cleavage and recovery (%) was estimated by counting of gel slices and is reported for 2 hr for hydroxylamine cleavage and 30 min for osmium tetroxide. Recovery was calculated in relation to an unincubated control.

RESULTS

Hydroxylamine Cleavage of Mismatched C

The concentration and pH of exposure to the reagent were chosen from preliminary experiments. These indicated that optimal cleavage was obtained after incubation for 2 hr with 2M hydroxylamine at pH6 compared with pH 5 and 7. Lower concentrations were not as effective, and longer times led to the destruction of the DNA.

Figure 2A:
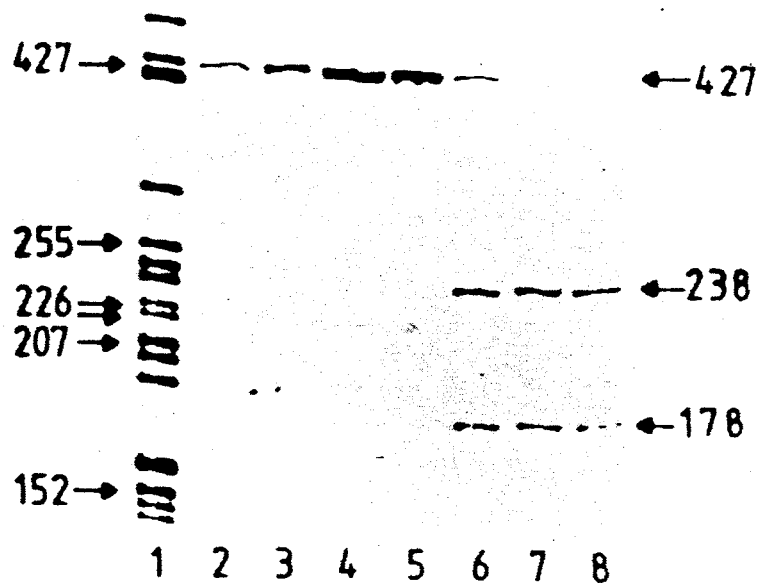
FIG. 2 illustrates the results of reaction of hydroxylamine with: (A) a C/C mismatch (mutation B8), (B) C/A and C/T mismatches (mutations B4 and B3, respectively), and (C) a C/A mismatch (mutation B11) using internally labelled probe.

The results are shown in FIG. 2. In the Figure:

(A) Lanes 5, 6, 7 and 8 show the effect of increasing times of incubation (0, 30, 60 and 120 min. respectively) of 2M hydroxylamine at 37° C. with a heteroduplex containing C/C as the only mismatch. Controls of this incubation are lane 2, homoduplex with the same labelled strand but unlabelled wild type DNA incubated as for lane 8; lanes 3 and 4, as for lane 8 but without piperidine and hydroxylamine, respectively. The amount of DNA in tubes 2-8 was 1.2 ug. Numbers on the left hand side refer to size of the markers (lane 1) and those on the right the size of the fragments and original probe.

(B) Lanes 3, 6, 7, 8 show the effect of increasing times of incubation (0, 30, 60 and 120 mins. respectively) of 2M hydroxylamine at 37° C. on a heteroduplex containing C/A and C/T as the only mismatches. The band at 195 bases represents cleavage of the C. at the C/T mismatch and the band at 215 bases represents the cleavage at the C of the C/A mismatch only. Controls for this incubation are, lanes 1 and 2: the complementary heteroduplex with a G/T mismatch (the 5' mutant strand labelled and the wild type unlabelled DNA) incubated for 0 and 120 min. respectively. Lanes 4 and 5: as for lane 8, but without hydroxylamine and piperidine, respectively. The amount of DNA in tubes 2-8 was 2 ug.

(C) Lanes 4, 5, 6, 7 show the effect of increasing times of incubation (0, 30, 60 and 120 min, respectively) of 2M hydroxylamine at 37° C. with a heteroduplex containing C/A as the only mismatch (except for ragged ends due to the presence of a small region of M 13 vector—see Table 1). The two products of the reaction can be seen as a result of the cleavage at the C of the C/A mismatch. The controls for this incubation are lane 1: homoduplex with the same labelled strand but unlabelled wild type DNA (Table 1) incubated as for lane 7, lanes 2 and 3: as for lane 7 but without piperidine and hydroxylamine, respectively. The amount of DNA in tube 2-7 was 0.3 ug. In (B) and (C) numbers on the right refer to size of the markers (lane 8) and those on the left the size of the fragments and original probe.

Figure 2B:
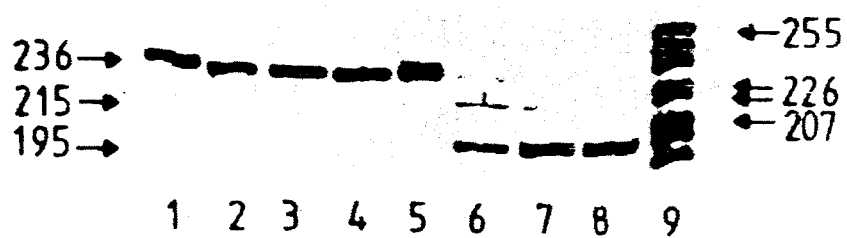
Figure 2C:
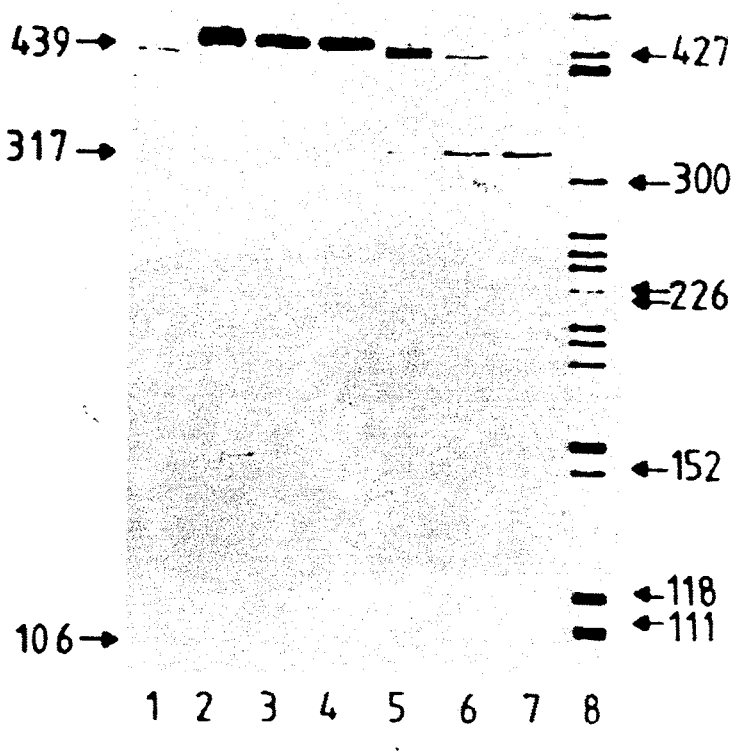

The cleavage of C/C, C/T and C/A mismatches (mutations B8, B4 and B11 respectively (6)), with increasing time are shown in FIG. 2. Cleavage at 2 hr was 93%, 88% and 74% with recoveries of 65%, 71% and 23%, respectively (recoveries of 70% were later constantly achieved by use of a methanol/dry ice bath for ethanol precipitation). The fragment at 215 bases in FIG. 2B is due to cleavage of a C/A mismatch (mutation B3) which lies 20 bases from the C/T mismatch. Cleavage at this C/A mismatch was not quantitated. In all cases the size of the cleavage products was consistent with cleavage at the respective mismatches. Controls with no incubation, hydroxylamine or piperidine, a homoduplex with the same labelled strand, and a heteroduplex with the opposite strand labelled showed no specific cleavage (FIG. 2). In the study of mutation B11 (C/A mismatch) the probe included 10 bases of the vector and the size heterogeneity seen in FIG. 2C (lane 5) is due to cleavage of those unpaired bases.

The above results are consistent with cleavage at the position of the mismatch concluded from sequencing studies (6), but do not prove that it is at this point. To determine the exact position of cleavage the 3' end of probe VI was end-labelled using Klenow.

Figure 3:
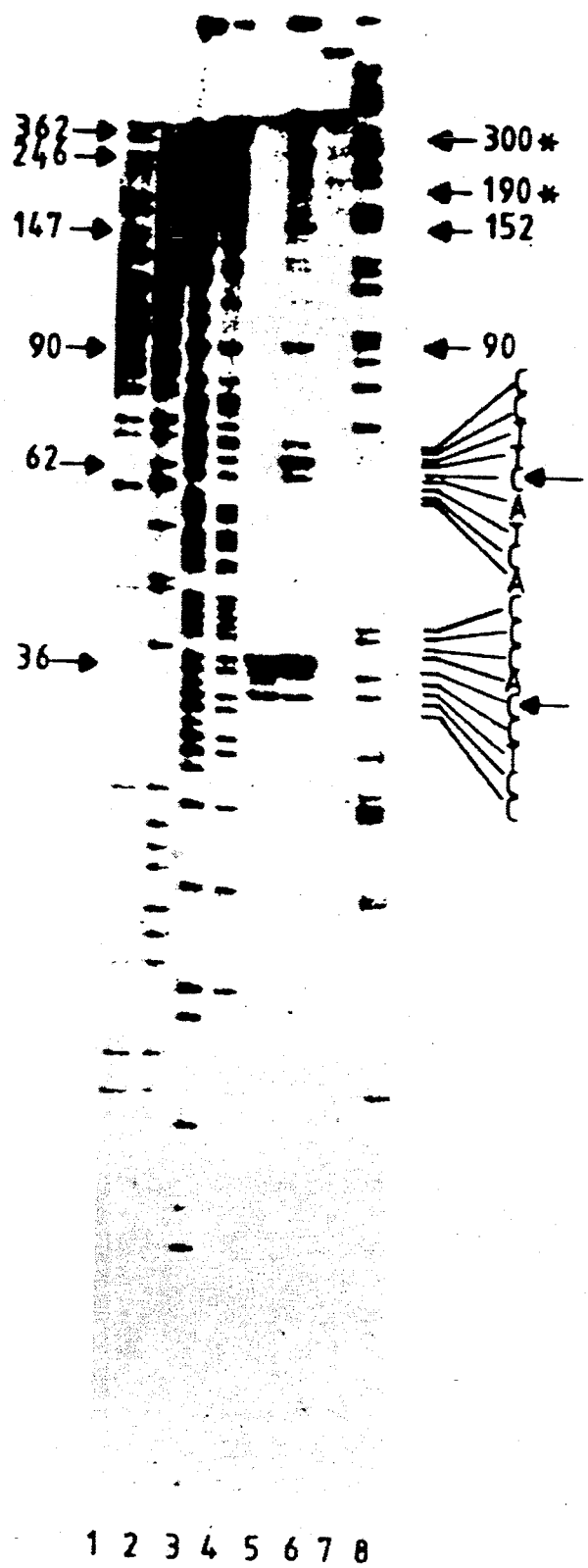
FIG. 3 is an analysis of cleavage of a heteroduplex by hydroxylamine using end labelled DNA.

The results are shown in FIG. 3. In this Figure lanes 1-4 show a Maxam and Gilbert sequencing ladder of the end-labelled probe (region VI) (G, A, T and C, respectively). Lane 5 shows the same labelled DNA after formation of a heteroduplex control with 12 times excess unlabelled mutant DNA (Table 1) and reaction with 2M hydroxylamine for 2 hrs at 37° C. Lane 6 shows the same labelled DNA after formation of a heteroduplex with 12 times excess unlabelled A gene DNA and reaction with 2M hydroxylamine for 30 min at 37° C. Lane 7 shows the same labelled DNA used for the formation of a homoduplex control with 12 times excess unlabelled wild type DNA and reaction with 2M hydroxylamine for 2 hrs at 37° C. To the right are shown the sequences around two of the cleavage points (arrows) where the sequence is readable. Numbers on the left are the sizes of fragments (and probe) produced by the heteroduplex shown in lane 6. Numbers on the right are the sizes of markers (lane 8). The amount of DNA in tubes 5-7 was 2.2 ug.

The product of the cleavage reaction is exactly adjacent to the mismatched C (FIG. 3 lane 5). Two faint products one and three bases from the mismatched C are also apparent presumably due to propagation (10) where paired C's near the mismatch show some reactivity with hydroxylamine, similar to the case of loops in tRNA studies.

The ability of hydroxylamine and piperidine to cleave C mismatches in different sequence contexts is summarised in Table 1. Cleavages of 90%, 84% and 87% were observed for a C/C mismatch (mutation B5) and 2 C/A mismatches (mutations B1 and A82a), respectively. In other cases only the ability to cleave was recorded.

Screening of a larger number of mismatches for cleavage was possible in the probe IV/V region (see FIG. 1) making use of the large number of differences between the 21-OHase A and B genes in this area. End-labelled probe was used to facilitate the positioning of cleavage and partial cleavage with hydroxylamine was used to increase the yield of the various bands expected. One such experiment is illustrated in FIG. 3 (lane 6) using a probe from region VI hybridised to the unlabelled 21-OHase A gene DNA. Labelling was at the 3' end of the sense strand. After partial (30 min) reaction with hydroxylamine all and only the expected size species of 246, 147, 90, 62 and 36 bases are seen. This is consistent with cleavage at the 5 expected mismatched C's: C/A, C/T, C/T, C/C and C/C, respectively (mutations A24, A35, A45, A48 and A50). One mutation (A48) did not produce an isolated C mismatch due to the presence of a T/C mismatch immediately adjacent.

Use of a probe from region X (FIG. 1) potentially allows the study of 8 mismatched C's and one unpaired C, while use of a probe from region XI (FIG. 1) potentially allows the study of 11 mismatched C's and one unpaired C in a loop. Table 1 shows those cleavages where neighbouring mismatches are more than 3 bases away. In both these cases in the regions able to be assessed all mismatched or unpaired C's were cleaved.

Besides those C's near the mismatched C's which showed lesser cleavage, presumably due to propagation, no unexpected cleavages were found.

Osmium Tetroxide Cleavage of Mismatched T

Figure 4A:
FIG. 4 illustrates the results of reaction of osmium tetroxide with (A) a T/G mismatch (mutation B3), (B) a T/C mismatch (mutation B4), and (C) a T/T mismatch (mutation A64) using internally labelled probe.
Figure 4B:
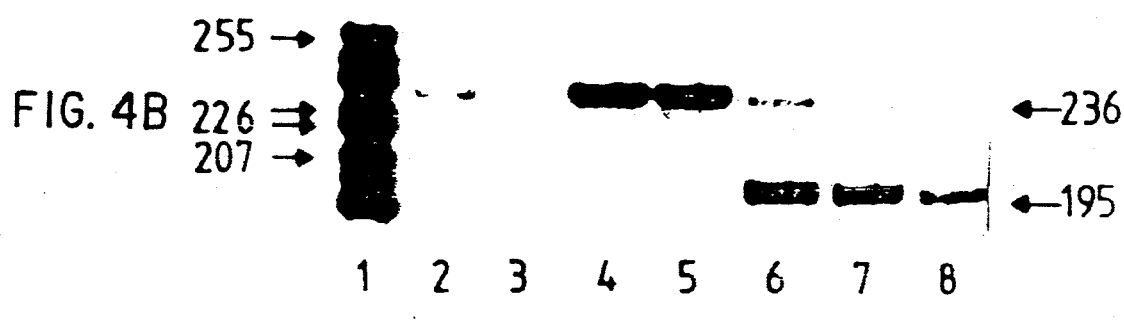
Figure 4C:

The cleavage of T/G, T/C and T/T mismatches (mutations B3, B4 and A64, respectively) are shown with increasing time in FIG. 4. In the Figure.

(A) Lanes 4, 5, 6 and 7 show the effect of increasing times of incubation (0, 30, 60 and 120 min respectively) with 2.4% osmium tetroxide at 37° C. with a heteroduplex containing T/G and A/G as the only mismatches Controls for this incubation are: lane 2, homoduplex with the same labelled strand, but unlabelled wild type DNA incubated as for lane 7. Lane 3, as for lane 7, but without osmium tetroxide. The amount of DNA in tubes 2-7 was 0.08 ug.

(B) Lanes 5, 6, 7 and 8 show the effect of increasing times of incubation (0, 15, 30, 60 min. respectively) with 2.4% osmium tetroxide at 37° C. on a heteroduplex containing T/C and A/C as the only mismatches Control for this incubation are lane 2: homoduplex with the same labelled strand, but with unlabelled wild type DNA incubated as for lane 7. Lanes 3 and 4: as for lane 8 but without piperidine and osmium tetroxide, respectively. For lanes 3 and 4 only half the DNA was loaded. All tubes contained 0.35 ug DNA.

(C) Lanes 5, 6, 7, 8 show the effect of increasing times of incubation (0, 15, 30, 60 min respectively) with 2.4% osmium tetroxide at 37° C. with a heteroduplex containing T/T as the only mismatch. The two products of the reaction can be seen as a result of cleavage at the T/T mismatch. The controls for this incubation are lane 2: homoduplex with the same labelled strand, but unlabelled wild type DNA incubated as for lane 8. Lanes 3 and 4: as for lane 8, but without piperidine and osmium tetroxide, respectively for lanes 3 and 4 only half the sample was loaded. All tubes contained 0.19 ug DNA. In all cases the numbers on the left refer to the size of the marker fragments (lane 1) and those on the right to the size of the fragments and original probe.

Cleavage was 61%, 78% and 17% with recoveries of 33%, 30% and 21% respectively. Controls without incubation, osmium tetroxide, piperidine, or using a homoduplex showed no specific cleavage. In all cases the size of the cleavage products was consistent with cleavage at the respective mutation.

Table 1 shows a summary of the results obtained with further examples of the three T mismatches studied with internally labelled probe. Substantial cleavage of the probes used was observed in the case of single examples of T/G (mutation B10a) and T/C (mutation A65) mismatches. Cleavage of T mismatches that were not quantitated were studied with end labelled probe (see below). Two further examples of cleavage of each of T/G and T/C mismatches (mutations A17, A23, A29, A30) can be seen in FIG. 5 (Table 1). Three further examples of T/G mismatches (mutations A46, A84, A88) and an example of a T/T mismatch (mutation A31) were cleaved in other end labelled probes (Table 1).

Figure 5:
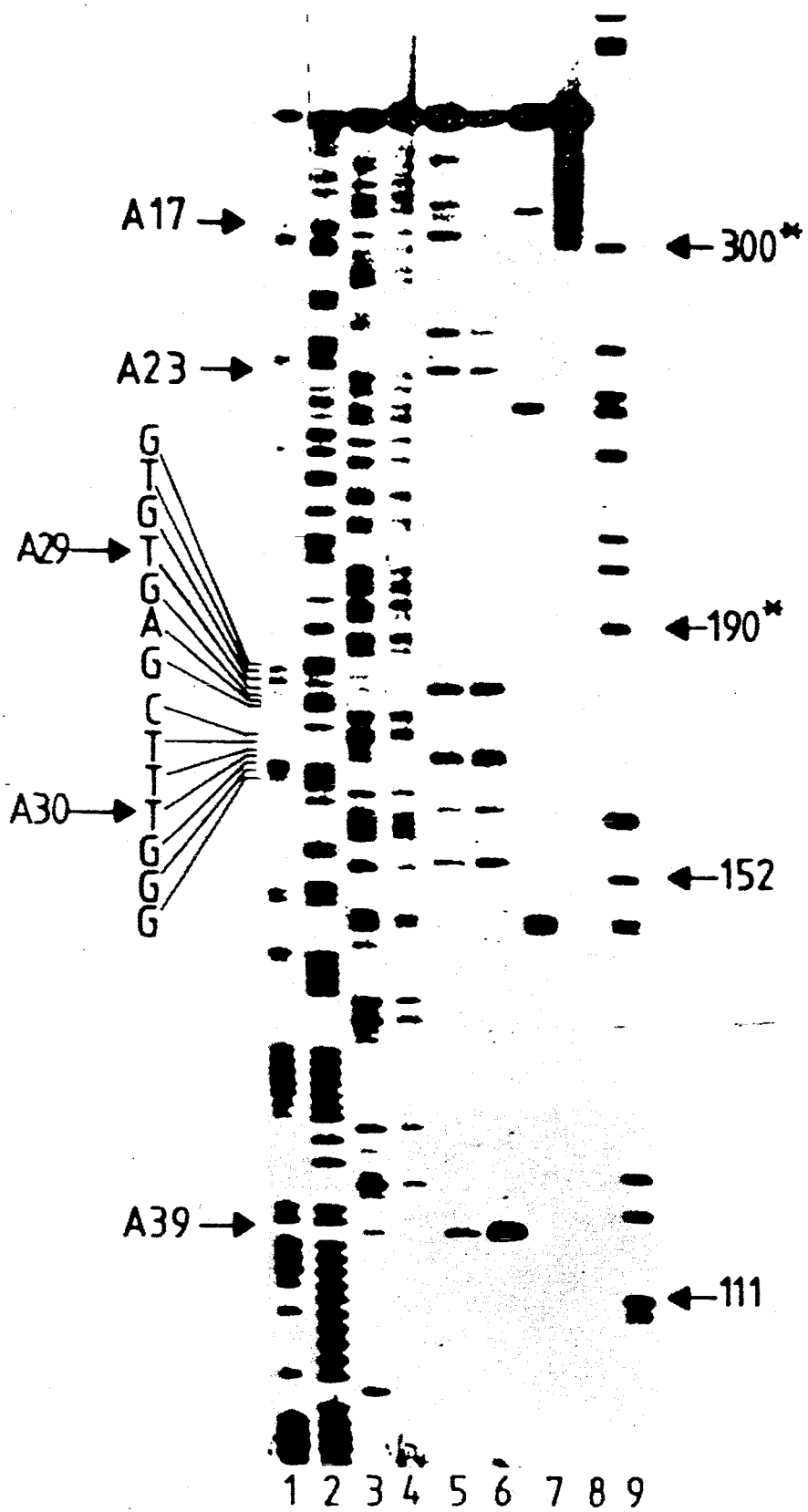
FIG. 5 is an analysis of the position of cleavage of the heteroduplex shown in FIG. 3 by osmium tetroxide as well as hydroxylamine using end labelled DNA.

To determine the exact position of cleavage the Maxam and Gilbert sequencing ladder of end-labelled probe was run next to heteroduplex reacted with osmium tetroxide (FIG. 5, lanes 1-6). It can be seen that the two isolated T mismatches (A29 and A30) are cleaved at the position of the mismatch.

FIG. 5 also illustrates the use of end labelled probe in a heteroduplex with cold DNA suspected of containing sequence changes and partial cleavage is a convenient method for detection of these differences. Lanes 1-4 show a Maxam and Gilbert sequencing ladder of the end-labelled probe (region VI) (G,A,T and C, respectively). Lanes 5 and 6 show the same labelled DNA after formation of a heteroduplex with 12 times excess unlabelled mutant DNA (Table 1) and reaction with 2.4% osmium tetroxide for 1 and 5 min, respectively, at 37° C. Lane 7 shows the same DNA heteroduplex treated with 2M hydroxylamine for 10 min at 37° C. Lane 8 is a homoduplex control with the same labelled strand but with wild type unlabelled DNA treated with 2.4% osmium tetroxide for 5 min at 37° C. To the left are shown the sequences around two of the cleavage points (arrow) where the sequence is readable. Letters and numbers on the left are the mutation numbers represented by the cleavages in lanes 5 and 6 and numbers on the right are the size of the markers (lane 9). The amount of DNA in tubes 5-8 was 2.6 ug.

After a short incubation with osmium tetroxide (FIG. 5, lane 5-1 min, lane 6-5 min) and subsequent cleavage of the heteroduplex with piperidine a number of bands not seen in the homoduplex control treated in the same way (FIG. 5, lane 8) are apparent. Consideration of the sequencing tracks (Lanes 1-4), the molecular weight markers (FIG. 5, lane 9) and the sequence allows assignment of the bands to specific T bases. The 5 single base pair mismatched T's are indicated by mutation name and lead to 5 of the 6 strongest bands seen in lane 5. The sixth strong band (second from top) is due to the cleavage of a T next to a loop in the 21-OHase A gene due to insertion of 4 bases in this gene. The next strongest bands, two below mutation A30, are due to cleavage of mismatched T's next to a single base pair mismatch (mutation A31) or 3 bases from a 3 base insert. Three further examples of the former are seen in the 3 faint bands above mutation A29.

The faint band below mutation A23 (FIG. 5, lanes 5 and 6) and at the second hydroxylamine cleavage of C from the bottom (Lane 7) is consistent with slower cleavage of C mismatches by osmium tetroxide than T mismatches (see below).

The hydroxylamine cleavage of the same heteroduplex (FIG. 5, lane 7) (also illustrated in FIG. 3, lane 6) illustrates how a stretch of DNA can be scanned for all T and C mismatches.

Osmium Tetroxide Cleavage of Mismatched C

The C mismatches previously studied for cleavage by hydroxylamine/piperidine were also studied for cleavage by osmium tetroxide/piperdine (Table 1). Using internally labelled probe with C/T, C/C, and C/A mismatches (mutations B4, B8, B1), cleavages of 57, 78 and 81% respectively, were found. A further 2 C/A mismatches (mutations B3 and B11) were also cleaved, but the values were not quantifiable. The rate of cleavage of the C mismatches by osmium tetroxide was slower than cleavage of T mismatches (not shown).

Discussion

We have screened a variety of reagents for their ability to react with purine or pyrimidine bases when they are mismatched in a duplex in such a way that the probe containing the mismatched bases is cleaved at that point by piperidine. Such reagents included hydrazine, potassium permanganate, formic acid, sodium hydroxide, diethyl pyrocarbonate, methylene blue, hydroxylamine and osmium tetroxide and have been used for structural studies of tRNA (7, 10), sequencing (8) and zDNA studies (11). Two reagents, hydroxylamine (12, 13, 14) and osmium tetroxide (12) were the only ones which showed promise and conditions were established for maximal cleavage of mismatched C and T, respectively (data not shown). We applied these conditions to a large number of T and C mismatches and showed that all 13 T mismatches studied were cleaved and these included 2 T/T, 4 T/C and 7 T/G mismatches. All 21 C mismatches studied were also cleaved and these included 2 C/C, 7 C/T and 12 C/A mismatches. At least one example of each C mismatch was cleaved with osmium tetroxide at a slower rate consistent with earlier studies (15). Previous work on tRNA using osmium tetroxide (16) and O-methyl hydroxyamine (17), a compound related to hydroxylamine, allowed us to predict that unmatched C or T would be reactive and this was shown in 3 cases of unmatched C's (data not shown). Thus all types of mutations, i.e. insertions, deletions and base changes, can be detected by the method of the invention.

The use of end labelled probes (FIGS. 3 and 5) allowed us (a) to confirm that for selected cases the point of cleavage by the reactions was at the point predicted by previous sequencing studies, (b) to collect further examples of C or T mismatch cleavages, and (c) to use the above findings to test a mode which could be used in practice to detect mismatches and hence mutations/polymorphisms after wild type (or reference) DNA had been annealed to variant DNA.

The method for detection of mismatched bases described here as applied to cloned DNA can be contrasted with two recently described methods. The ribonuclease method (3, 4) needs an extra step of cloning (into the SP6 vector) beyond that needed for the carbodiimide method (5) or the method described here. However, the greatest drawback of the ribonuclease method appears to be the variable cleavage of some mismatches ranging from none of six G/C mismatches through one of fourteen G/T and one of seven G/A mismatches to excellent cleavage of all 22 C/A mismatches (3). The study of mismatches with end labelled probe is theoretically possible with the ribonuclease method, but has not yet been reported. The carbodiimide method needs the heteroduplex to be made blunt ended before reaction, but its potential scope is unclear in terms of detectability as the results for only two mismatches were given (T/C and G/T), with positive results for G/G amd T/T mismatches being mentioned without data being shown. This method being a non cleavage method clearly cannot be used in the "ladder mode".

EXAMPLE 2

There is a need to ascertain the genetic variability among isolates of RNA (or DNA) viruses in epidemiological surveys, to type new isolates in disease outbreaks, and to characterise laboratory isolates generated by recombination or selection with neutralizing monoclonal antibodies.

There are four serotypes of dengue virus, types 1 to 4.

The genome of the virus is single-stranded RNA of positive polarity, approximately 11 kilobases in length. The genomes of dengue virus types 2 and 4 have been completely sequenced (18-20) Three isolates of dengue virus type 2 were examined in this study. They were the prototype virus New Guinea C (NGC) (21) and two strains isolated during 1980 in Bangkok, designated PUO-218 and D80-100 (22). The coding regions for the structural glycoproteins prM and E of NGC and PUO-218 viruses have been cloned and the cDNA sequenced by chain termination method (23). D-80-100 virus has not been sequenced.

MATERIALS AND METHODS

Cloning of virus cDNA has been reported previously (23, 24).

Formation of DNA/DNA heteroduplexes, the partial cleavage of mismatched T and C bases and their electrophoretic analysis were carried out as described in Example 1 except the osmium tetroxide solution used in these experiments was further diluted 1 in 5.

Isolation of viral RNA from purified virions and infected Vero cells have been previously described (24, 25). Formation of DNA/RNA heteroduplexes was performed in 80% formamide, 40 mM PIPES pH 6.5, 1 mM EDTA and 400 mM NaCl at 90° C. for 5 minutes, 55° C. for 60 minutes, reducing to 45° C. over 60 minutes and finally at 45° C. for 60 minutes. Each tube contained 0.34 ug of purified viral RNA with 3.9 ug of sonicated salmon sperm DNA, or 5 ug of total infected cell RNA. Base modification and displacement reactions were as previously described (26).

RESULTS

An end-labelled probe of negative sense PUO-218 within the coding region for the structural glycoproteins was prepared (FIG. 6).

In FIG. 6 the first nucleotide corresponds to nucleotide 471 in the published NGC sequence (23). The probe (nucleotides 6 to 453) used in all experiments was prepared from a 2.1 kilobase cDNA insert of PUO-218 in pUC8 by digestion with Nco I and Hind II. Negative-sense cDNA was end-labelled at the 3' end. The start points of the coding regions for the structural proteins M and E, and the positions of mismatched C (*) and T (+) in the probe are marked. Additional bases susceptible to chemical cleavage are indicated by a solid circle.

The probe was annealed in turn to unlabelled NGC and PUO-218 cDNA for the same region, to positive-sense viral RNA extracted from purified virions of the three viruses and to total cell RNA extracted from NGC virus-infected Vero cells. DNA/DNA and DNA/RNA heteroduplexes were cleaved at mismatched C and T bases.

Figure 7:
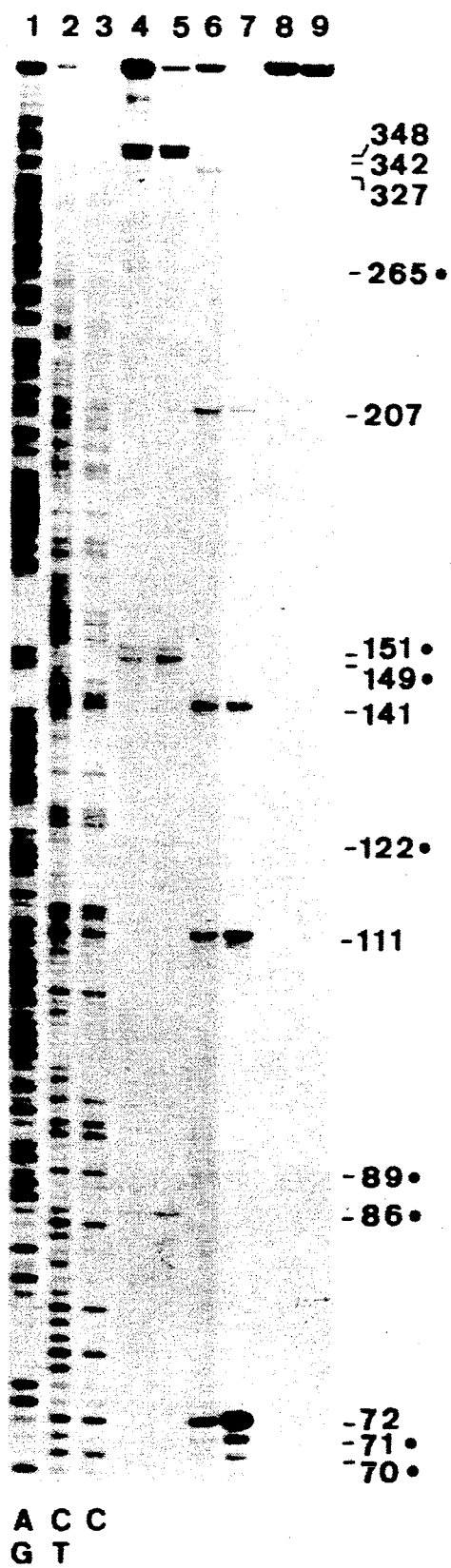
FIG. 7 is an analysis of mismatches using a labelled PUO-218 probe of negative-sense hybridized with unlabelled NGC and PUO-218 cDNA.

FIG. 7 shows the results for the DNA/DNA heteroduplexes. The probe alone was treated with Maxam and Gilbert reagents (lanes 1 to 3). Numbers on the right of FIG. 7 represent base numbers as defined in FIG. 6 and are positioned at point of cleavage. Numbers marked with a solid circle represent cleaved bases near mismatches. Lanes 4 and 5 show heteroduplexes (PUO-218/NGC) treated with osmium tetroxide for 1 and 5 minutes respectively. Lanes 6 and 7 show heteroduplexes treated with hydroxylamine for 10 and 60 minutes respectively. Lanes 8 and 9 show homoduplexes (PUO-218/PUO-218) treated with osmium tetroxide for 5 minutes or hydroxylamine for 60 minutes respectively. The seven predicted mismatched base pairs containing a C or T in the end-labelled probe were all detected. Additional limited cleavages adjacent to some C/A and G/T mismatches were also apparent, for example at bases 71, 86, 89, 149, 151, 265, 341 (adjoining mismatches), and at bases 70 and 122 (two bases removed from a mismatch).

Figure 8A:
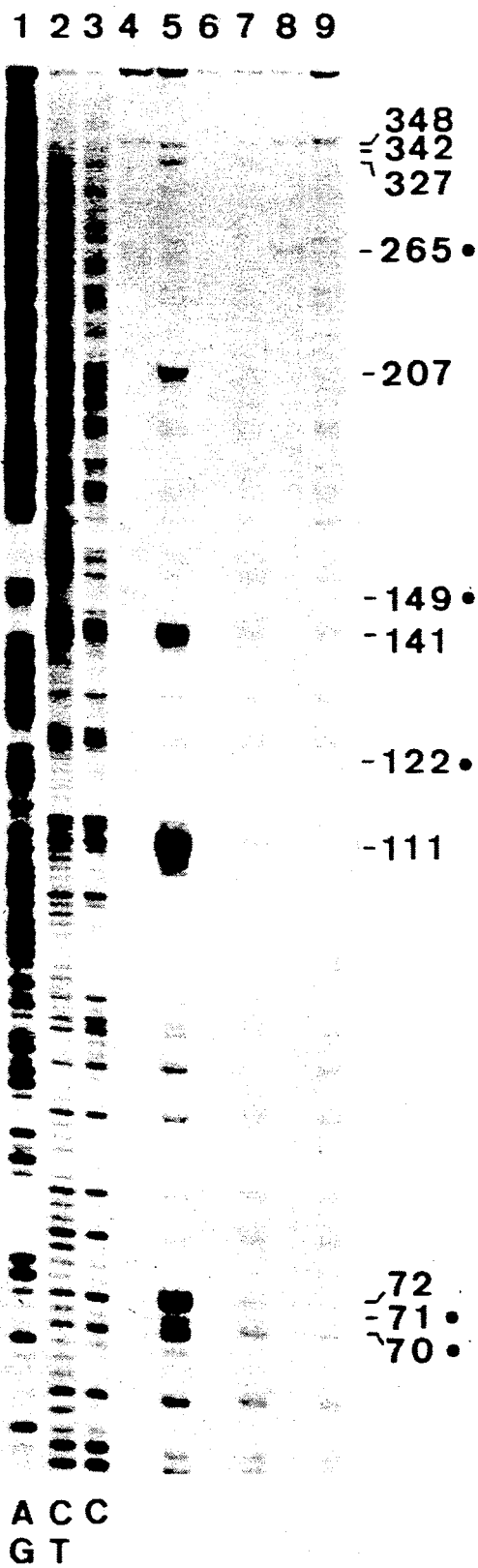
FIG. 8 is an analysis of mismatches using a labelled PUO-218 cDNA probe of negative-sense hybridized with unlabelled RNA isolated either (a) from purified virions, or (b) from virus-infected Vero cells. The probes in (a) and (b) were treated with Maxam and Gilbert reagents (lanes 1 to 3)
Figure 8B:
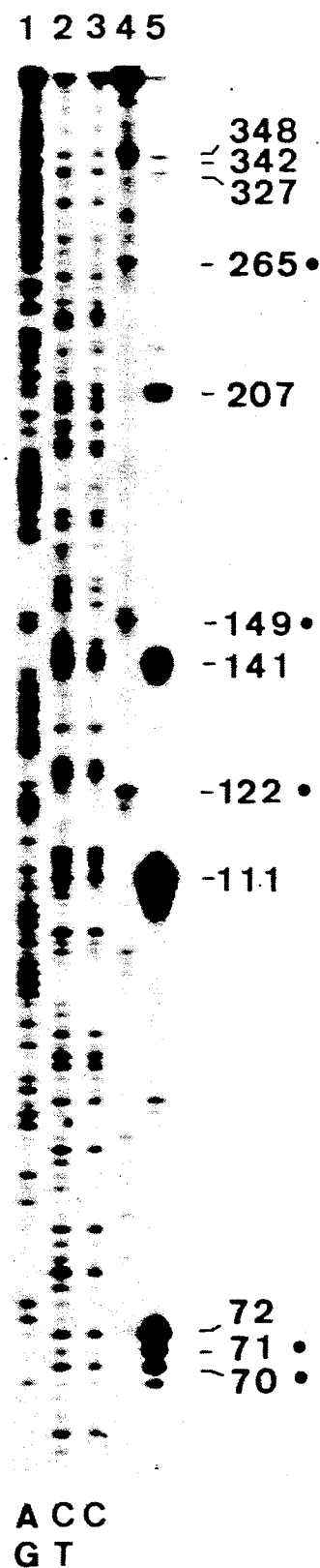

FIG. 8 shows the results for the DNA/RNA heteroduplexes. Lanes 4 and 5 in FIG. 8(a) show heteroduplexes of probe (PUO-218) and NGC RNA, lanes 6 and 7 show homoduplexes of probe and PUO-218 RNA and lanes 8 and 9 show heteroduplexes of probe and D80-100 RNA. Lanes 4, 6 and 8 represent treatment with osmium tetroxide for 5 minutes and lanes 5, 7 and 9 treatment with hydroxylamine for 60 minutes. Lanes 4 and 5 in FIG. 8(b) are heteroduplexes of probe and RNA from cells infected with NGC virus treated with osmium tetroxide for 5 minutes or hydroxylamine for 60 minutes respectively. Again all seven mismatches between PUO-218 and NGC were detected using purified viral RNA or total RNA extracted from infected cells. As in FIG. 7 a background of additional cleavages enriched the gel pattern and provided further information on the similarity or otherwise of the sequences under consideration. Three differences between D80-100 and PUO-218 viral RNA were detected, two in the region of bases 342–348 and one at base 263 (FIG. 8a, lanes 8 and 9). Clearly the sequence of the D80-100 virus more closely resembled that of PUO-218 rather than that of NGC.

DISCUSSION

The mismatches C/A, C/T, C/C and T/G, T/C, T/T in DNA/DNA heteroduplexes have been detected using hydroxylamine and osmium tetroxide respectively (26). We have not systematically examined all the corresponding mismatches in DNA/RNA heteroduplexes for chemical cleavage initiated by these reagents, but have demonstrated their potential to do so. It is clear that C/A (six examples) and T/C in single base pair mismatches are cleaved. Matched T or C bases near mismatches are also reactive allowing indirect detection of mismatched A and G in the probe. This indirect detection in this analysis accounted for 5 of 13 G and A mismatches. These combined reactivities indicated the presence of at least 12 of the 20 mismatches predicted by comparison of sequences of cDNA for two of the dengue strains. As the reagents are used more widely, information on the susceptibility of the bases within and adjacent to mismatched base pairs will accumulate. A feature of this approach is the ability to focus on a specific region of a genome by choosing an apropriate cDNA probe. In some instances, such as epidemiological surveys, a "fingerprint" of differences for a region using a probe of one sense only may be sufficient. The use of DNA probes of positive-sense will enable the detection of mismatched T and C in heteroduplexes with negative-sense RNA extracted from infected cells. Combining the results obtained with DNA probes of both sense may locate every point mutation in the region covered by the probes. To analyse the complete coding sequence for the E glycoprotein, ($M_r$ 60,000) of a new dengue isolate, three probes approximately 500 bases long and of both sense would be required.

Using this technique, differences involving T and C mismatches in the probe between NGC and PUO-218 were apparent by nucleotide sequencing. Thus the technique allowed proof reading of the published sequences. The closer relationship of the unsequenced D80-100 to PUO-218 rather than to NGC was demonstrated without the need to sequence D80-100. It is notable that the pattern obtained with the cloned DNA and cellular RNA of NGC are identical indicating that only one major strain is present in the cells and this had been cloned. We have demonstrated and applied the method of the invention for detecting variation in viral RNA in a genomic region of interest. The feasibility of using total infected-cell RNA in place of purified viral RNA for screening large numbers of isolates, and the potential to map point mutations are further advantages of the technique.

EXAMPLE 3

Materials and Methods

Figure 9:
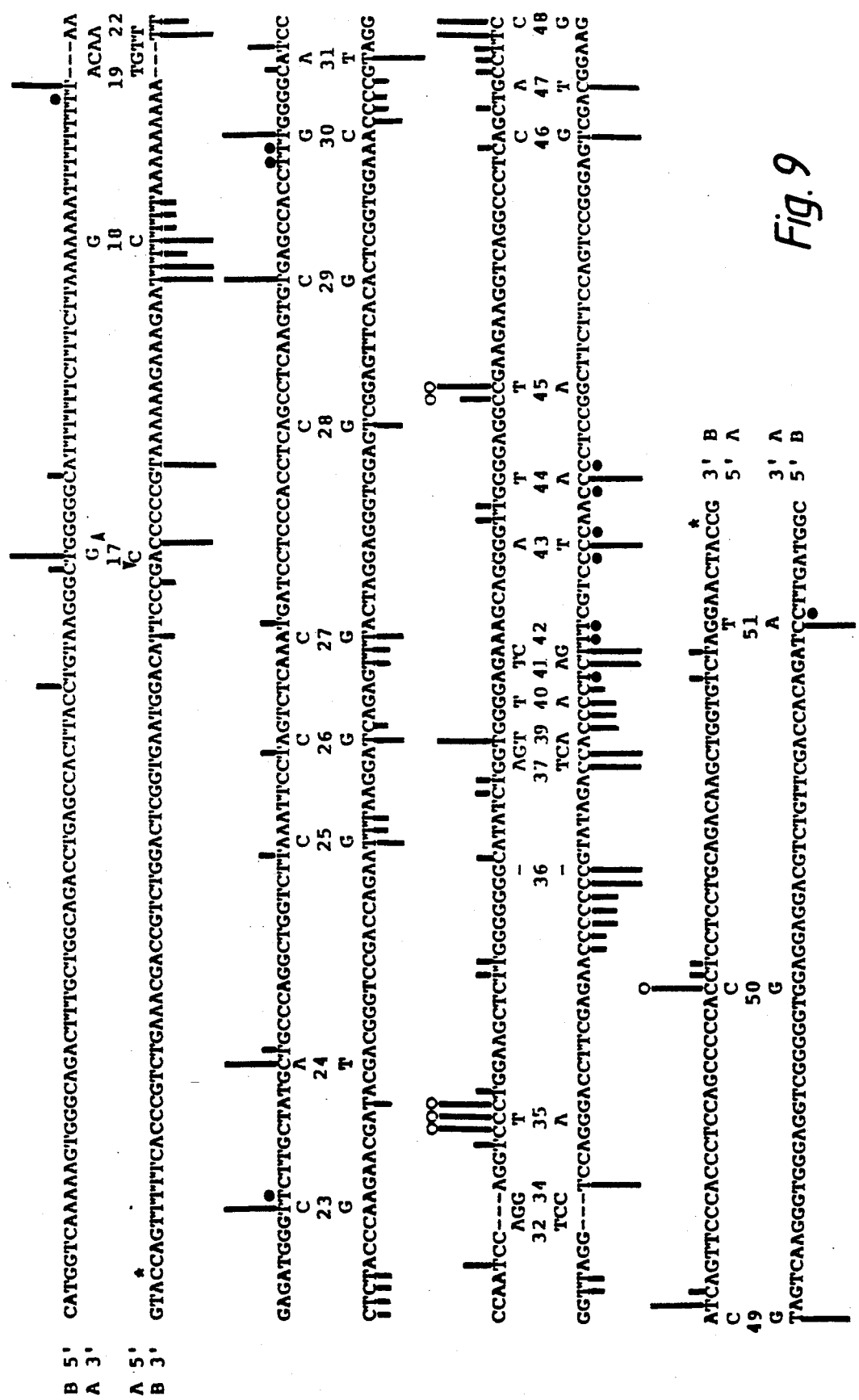
FIG. 9 shows the sequence of the portion of the 21 hydroxylase B gene (NcoI/MspI fragment) used in Example 3.

The source of DNA has been described in Example I. All studies were made using the 357 bp MspI/NcoI fragment of the 21 hydroxylase B gene (Rodrigues et al (6)) for the production of probes of both senses by end labelling using the method described in Example 1. Heteroduplexes were formed with MspI/NcoI digests of the 21 hydroxylase A pseudogene (Cotton et al (26)). The 363bp region studied is shown in FIG. 9. The 21 hydroxylase A gene differs in 35 positions (including 6 base insertions) from the 21 hydroxylase B gene in this region.

FIG. 9 shows the sequence of the portion of the 21 hydroxylase B gene used, and the bases which differ in the 21 hydroxylase A gene are also shown. The sequences are paired as they would be in the heteroduplex such that the actual mismatches, deletions and insertions created are indicated. Probes were made of the 21 hydroxylase B gene strands for both senses and hybridized with the unlabelled 21 hydroxylase A gene. Numbers above the sequence represent 21 hydroxylase A gene mutation number (Cotton et al, 6). Asterisks show the base used to label the strand. Each complete line contains 100 base positions. The arrows indicate the position of the MspI cut sites introduced into the 21 hydroxylase A gene by mutation A 17. Vertical lines above and below T and C bases represent the reactivity of that base with the appropriate chemical when the particular sequence is used as probe. Three lengths of these lines represent relative reactivity as judged from FIG. 10. Closed circles represent those bases which are probably reactive but the analysis cannot confirm it. Open circles represent C bases clearly reactive with osmium tetroxide.

Partial cleavage of the heteroduplexes was essentially as described in Example 1 and particular conditions are given in connection with the relevant Figures. Cleavage was assayed by electrophoresis on 8, 10 and 20% denaturing urea gels as described in Example 1.

Analysis of cleavage was by densitometry of the bands on the autoradiograph produced from the dry gel.

Maxam and Gilbert sequencing of the labelled probes was performed (Cotton et al (6); Maxam and Gilbert (8)) and samples were run next to the analysis to position the T and C residue being studied.

RESULTS

A probe of positive sense of the 21 hydroxylase B gene was labelled at the 3' end at the MspI site by end filling with Klenow and cut out with NcoI to create a probe of 357 basepairs (FIG. 9) This was then hybridized with the unlabelled 21 hydroxylase A gene using excess DNA to form a heteroduplex which contained a number of mismatched and unmatched bases and a single strand break which are shown in FIG. 9 and Table 2. Besides the mismatched bases there were two loops in the unlabelled strand due to insertions in the 21 hydroxylase A gene and one single base loop in the labelled strand due to a deletion in the 21 hydroxylase A gene. Mutation A17 creates an MspI site in the 21 hydroxylase A gene. Thus instead of the anticipated mismatch at this position a strand break was present in the unlabelled strand of the heteroduplex.

In Table 2 symbols have the following meanings:

(a): Mismatches at least 3 base pairs away from another mismatch, i.e. isolated mismatches are marked *.

C1 & T1: Indicate reactivity of C or T one base away from the mismatched base. If reactivity is substantial +++ appears aafter C1 and T1. A51 positive probe, data not shown.

+++ etc: Represents amount of reactivity of the T or C mismatch.

+Brackets Contiguous base changes are bracketed together.

N: Not applicable. In some cases C bases are reactive with osmium tetroxide (A36, 45, 50).

Heteroduplexes of end labelled 21 hydroxylase B and unlabelled 21 hydroxylase A gene were subject to limited cleavage by osmium tetroxide/piperidine and hydroxylamine/piperidine to study the reactivity of all the T and C bases in the labelled strands of the heteroduplexes, and the results are shown in FIG. 10 as autoradiographs and FIG. 11 as densitometer traces and are summarised in Table 2 and FIG. 9.

Figures 10A, 10B:
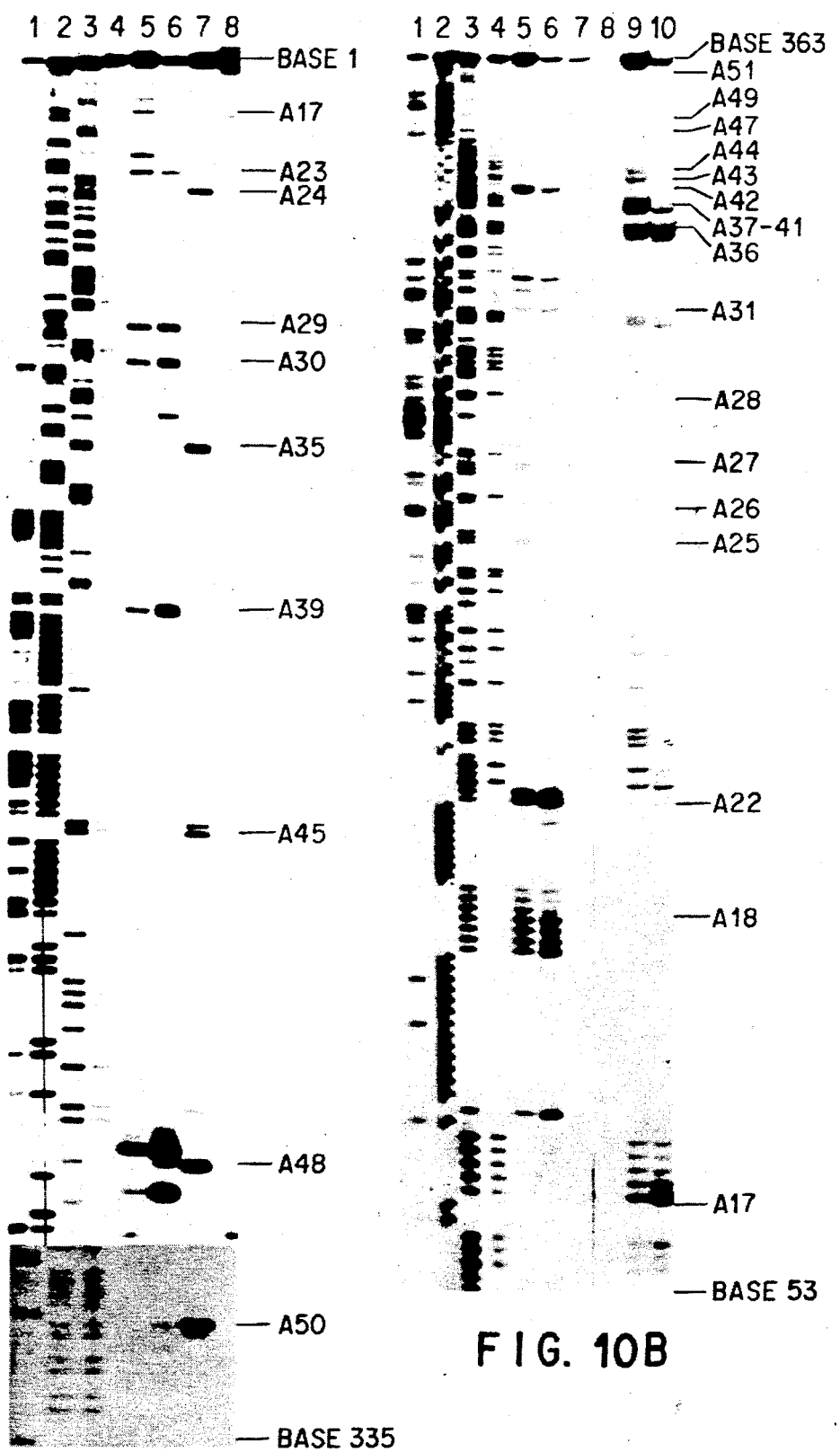
FIG. 10 is an autoradiograph analysis of fragments produced by partial cleavage of heteroduplexes of end labelled 21 hydroxylase B and unlabelled 21 hydroxylase A gene using osmium tetroxide and hydroxylamine.

FIG. 10a gives results for labelled sense strand of the 21 hydroxylase B gene hybridized with the 21 hydroxylase A gene. Lanes 1-4 Maxam and Gilbert sequencing tracks G, C +A, T+C and C respectively. Lanes 5 and 6 osmium tetroxide reaction for 1 and 5 minutes, respectively. Lane 7 hydroxylamine reaction for 10 minutes, lane 8 homoduplex control incubated for 5 minutes, with osmium tetroxide. Gels were 10% (top) or 20% (bottom) denaturing gels.

FIG. 10b gives results for labelled antisense strand of the 21 hydroxylase B gene hybridised with the 21 hydroxylase A gene. Lanes 1-4 Maxam and Gilbert sequencing tracks, G, G+A, T+C and C respectively. Lanes 5 and 6 osmium tetroxide reaction with heteroduplex for 1 and 5 minutes respectively. Lane 7 osmium tetroxide reaction with homoduplex for 5 minutes. Lane 8 hydroxylamine reaction with homoduplex for 60 minutes. Lane 9 and 10 hydroxylamine reaction with heteroduplex for 10 and 60 minutes respectively. Gel was an 8% denaturing gel.

In FIG. 11:

(a) Osmium tetroxide reaction with sense strand probe heteroduplex for 5 minutes (FIG. 10a, Lane 6).

(b) Hydroxylamine reaction with sense strand probe heteroduplex for 10 minutes (FIG. 10a, Lane 7).

(c) Osmium tetroxide reaction with antisense probe heteroduplex for 5 minutes (FIG. 10b, Lane 6).

(d) Hydroxylamine reaction wih antisense strand probe heteroduplex for 10 minutes (FIG. 10b, Lane 9).

In each case the T (a and c) or C (b and d) base positions are marked by a vertical line except where too many are present when a number is inserted between the lines to indicate the number of T and C bases. When particular T and C bases are mismatched or unmatched arrow heads are placed on the vertical line. When a particular T and C base is next to a mismatch, a point is placed on the bottom of the vertical line. Numbers under the vertical lines represent the position of mismatches etc formed from the A gene mutation of that number. In some cases numbers with arrow heads are placed away from the T and C bases to indicate relative positions of nearby mismatches. The bottom line of numbers represents the base number for the start of the 21 hydroxylase B gene segment under study (FIG. 9). Large arrow heads indicate the position of the break point due to the MspI site in the unlabelled 21 hydroxylase A gene. The vertical axis is relative band intensity.

As demonstrated earlier in Example 1 all mismatched T and C bases show cleavage. However many additional reactivities are present which are above "background". In this case background refers to the reactivity of normally matched T and C bases at least 3 bases from a mismatch. All T and C bases in the sequence of the probe are marked in FIG. 11 and can be located in FIG. 10 by the Maxam and Gilbert sequencing tracks except at the top of the gel where these bands are not well resolved.

The reactivity of the T bases with osmium tetroxide can be seen in tracks 5 and 6 of FIG. 10 and FIG. 11a (track 6). Four of the 9 strongest bands (other than uncleaved probe) are due to single base pair mismatched T residues A23, A29, A30 and A39. (The other mismatched T at the A17 break is not as reactive.) Three of the nine are matched T bases next to mismatches A31, A48 and A49. The matched T base next to insert A 19-21 is also very reactive and so is the T 3 bases from the A32-34 insert. Five matched T bases next to mismatches A24, A25, A26, A27 and A37 show less reactivity. Reactivity can also be seen of matched T bases each side of A35 and two matched T bases between A43 and A44.

The origin of the two bands above A17 (see lane 5) is difficult to ascertain particularly because of the lack of resolution of the bands in this area. The piece of unlabelled 21 hydroxylase A gene in the heteroduplex here is only 58 bases long (due to MspI cleavage—see above) and may account for higher background reactivity.

The broad band between A44 and A47 is due to reactivity of a mismatched C base (A45) and neighbouring C base with osmium tetroxide. The mismatched C base at A50 (FIG. 10a) also shows a little reactivity. Many matched T bases show little or no reactivity e.g. 4 between A27 and A29 and 1 between A45 and A46.

Figure 11B:
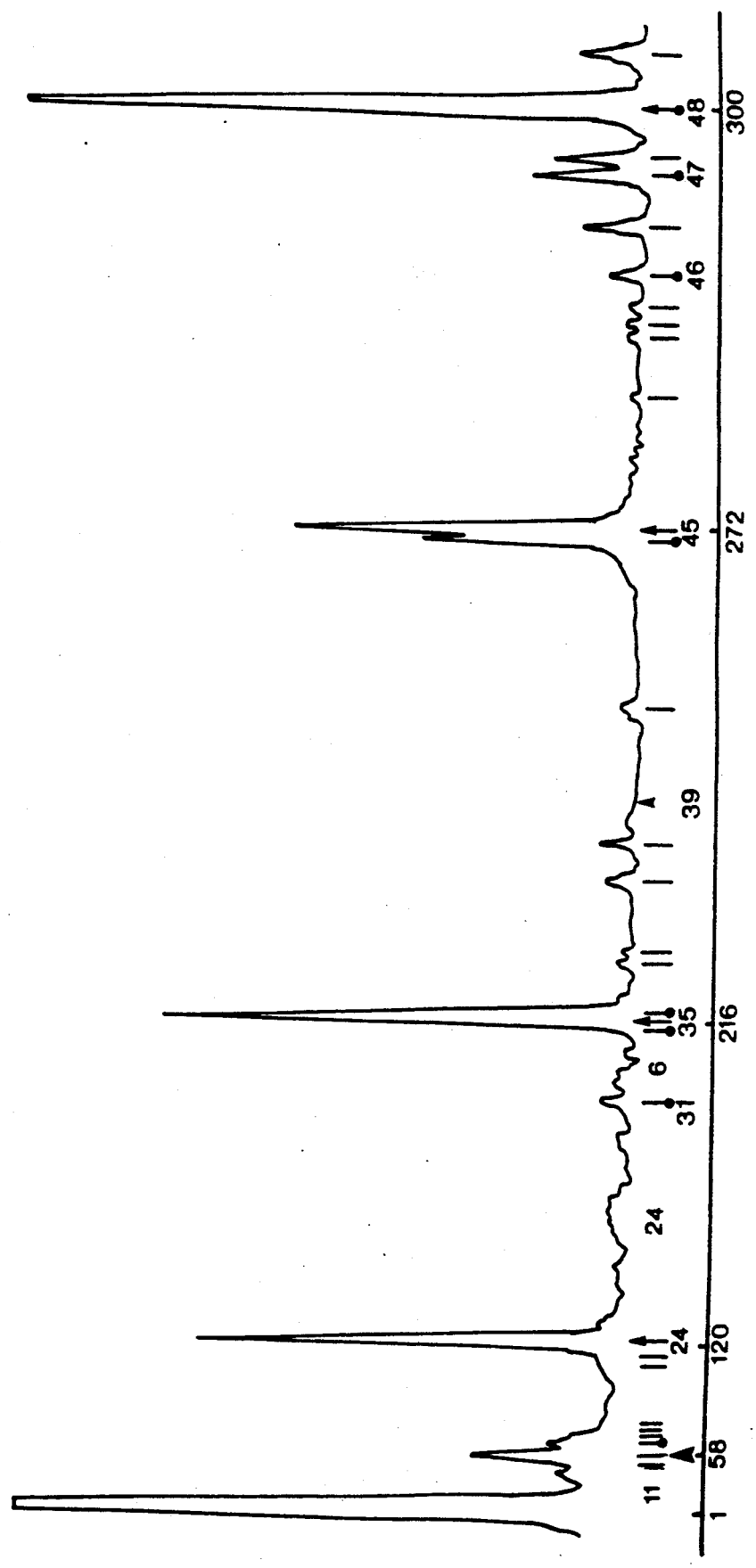

The reactivity of the C bases with hydroxylamine can be seen in track 7 FIGS. 10a and 11b. The four strongest bands are due to the reactivity of the four single base pair mismatched C bases (A34, A35, A45, A48). The next strongest band is that due to cleavage of the C base next to the A45 mismatch. At the position of the cleavage of the A35 mismatch, the width of the band indicates that possibly all 3 contiguous C's are reacting. The strong band above A24 may be due to the proximity of this C base to the break in the 21 hydroxylase A gene. The four bands above A48 and one below indicate increased reactivity and are close to the A46, A47, A48 and A49 mismatches. The C base next to A31 is also reactive. The two faint reactive bands above A39 are a C base near to A37-39 (2 bases) and another near A36 (a single G loop in the probe). Many matched C bases show little reactivity e.g. the 24 between A24 and A31.

The reactivity below A48 is shown only in FIG. 10a. No highly reactive T bases can be seen in this region. However a highly reactive C base can be seen in lane 7 close to the mismatched C base at A50, 38 base pairs from the end and a nearby C base is slightly reactive. It can be seen that the matched C base 31 bases from the end is not reactive. Below this (not shown) reactivity can be assessed up to base 354 (i.e. at A51, 10 bases from end) with T bases 350 and 352 showing some reactivity.

Homoduplex control for osmium tetroxide shows the top band (above A17) discussed above. None of the bands in track 6 are represented strongly in this track. No bands shown in the hydroxylamine reacted a homoduplex control (not shown).

The B gene probe of negative sense from the same piece of DNA was prepared by labelling the NcoI site and cutting out with MspI to create a probe again of 357 base pairs. A heteroduplex made with the 21 hydroxylase A gene as above with a number of unmatched and mismatched bases and loops as above (FIG. 9, Table 2). This heteroduplex was subjected to limited cleavage by osmium tetroxide/piperidine and hydroxylamine/-piperidine to study the reactivity of all the T and C bases in the heteroduplex corresponding to A and G bases in the first probe. The result of this experiment can be seen in FIG. 10b as an autoradiograph and in FIG. 11c and d as densitometer tracings and are summarised in Table 2 and FIG. 9.

The reaction of osmium tetroxide with the T bases in the heteroduplex can be seen in lanes 5 and 6, FIG. 10b. Lane 6 can be seen in FIG. 11c as a trace. T bases in isolated single base pair mismatches at A31, A28, A27, A26 and A25 all reacted with similar intensity. T bases 1 and 2 away from A27 and A25 were also reactive. The reactivity of A49 and A46 T base mismatches do not show distinctly in the scan of track 6 (FIG. 11c) but can be seen clearly in track 5, FIG. 10b at a lesser incubation time. (This phenomenon is discussed below.) The reactivity of T base mismatches at A42 and A22 are very high. The reaction around A18 which is found in an AT rich area is very high. The mismatch can be assigned to the A18 position as this T base has reacted more than T bases on each side (see below). The lone matched T base between the A18 and the break in the unlabelled 21 hydroxylase A gene at A17 in a very AT rich area is very reactive. The two strong bands above A31 and T bases each side of an insert (A32-34) in the unlabelled A gene DNA. A T base three bases from a mismatch at A24, shows reasonably strong activity. Many matched T bases show little or no reactivity e.g. 4 between A42 and A34.

The reactivity of the C bases in the labelled strand can be seen in tracks 9 and 10 FIG. 10b. Lane 9 can be seen as a scan in FIG. 11d. Two sets of strong bands in the top half are due to (a) reaction of a single C loop in the probe at A36 and the neighbouring four C bases and (b) the reactivity of seven C bases between A37 and A41 inclusive i.e. including five mismatches out of 9 bases. Clear bands can be seen for the isolated C base mismatches A43, A44 and A47. Reaction of A51 is not convincing but can just be seen below the "probe" band in lane 9 (FIG. 10b). The reactivity of several C bases next to the mismatch at A30 can be seen to be well above background.

Analysis of the products on a 20% gel (not shown) allows the reactivity of T and C bases to base 8 to be assessed with none showing enhanced reactivity. Matched C bases each side of A17 show relatively high reactivity. Almost all other matched C bases below A30 give a band under the reaction conditions. Usually those next to mismatches are more reactive than nearby matched C bases. Little reactivity is seen with 19 matched C bases between A44 and A51.

In both cases the homoduplex controls show very little reactivity (FIG. 10b, lanes 7 and 8).

DISCUSSION

The analysis of the data summarised in Table 2 and FIG. 9 supports the findings described in Example 1 that isolated mismatched T and C bases can be cleaved by alkali after treatment by osmium tetroxide and hydroxylamine respectively leading to detection of all classes of single base pair mismatches.

It is to be expected that the reactivity of single base pair mismatches may be variable due to the nature of the surrounding bases as the strength of binding between GC basepairs is stronger than the binding between AT basepairs. (Tinoco et al, 27). While the results of these experiments cannot be regarded as quantitative it is possible to draw some conclusions from them. The isolated T mismatches (at least 3 bases from another mismatch) A28 and A46 react relatively weakly. A28 (FIG. 11c) gives a signal weaker than nearby mismatched T bases (A31 and A27) possibly because it is in a GC rich area and has GC pairs on both sides, but it is still many times more reactive than nearby matched T bases on each side. A31 is in a GC rich area but has an AT base on one side whereas A27 is definitely in an AT rich area, so this may explain their relatively higher reactivity. A46 (FIG. 11c) may be weak because it is in an GC rich area and it has GC base pairs on each side. Thus it can be hypothesized that mismatches with GC base pairs on both sides may react more weakly. The reactivity of T base mismatches at A42 and A22 (FIG. 11c) are very high which is presumably due to A22 being next to an insert and A42 being next to another mismatch. This is also true for A39 (FIG. 11a). Thus it appears mismatches next to another mismatch are more reactive as perhaps expected.

Figure 11C:
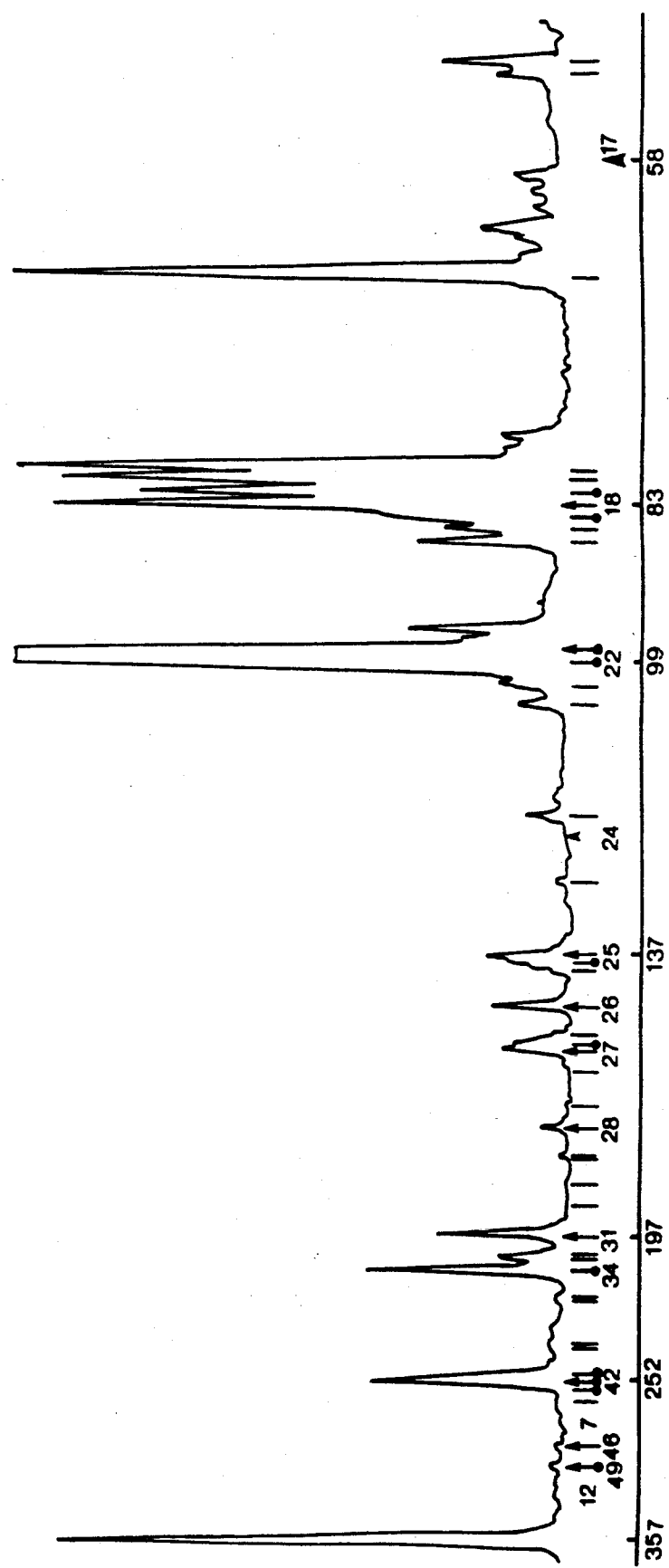

The relative reactivity of mismatched bases compared with reactivity of matched bases will be important in practical application of the method. The reactivity at the A46 mismatch (FIG. 11c) is small but is obviously higher than nearby matched T bases. The band can be seen more readily in the 1 minute osmium tetroxide incubation (FIG. 10b, lane 5) where this band is more prominant. The nearby A49 T base mismatch should be relatively reactive as it is next to another mismatch. Again the signal is enchanced in the 1 minute osmium tetroxide incubation indicating the importance of time course experiments. Detection of T base mismatches could be difficult in a run of matched T bases. This possibility can be examined in mutation A18 as in the antisense strand the mismatched T base has 3 T bases each side. Thus are all reactive but it can be seen the mismatched T base is more highly reactive than these on each side (FIG. 11c).

Figure 11D:
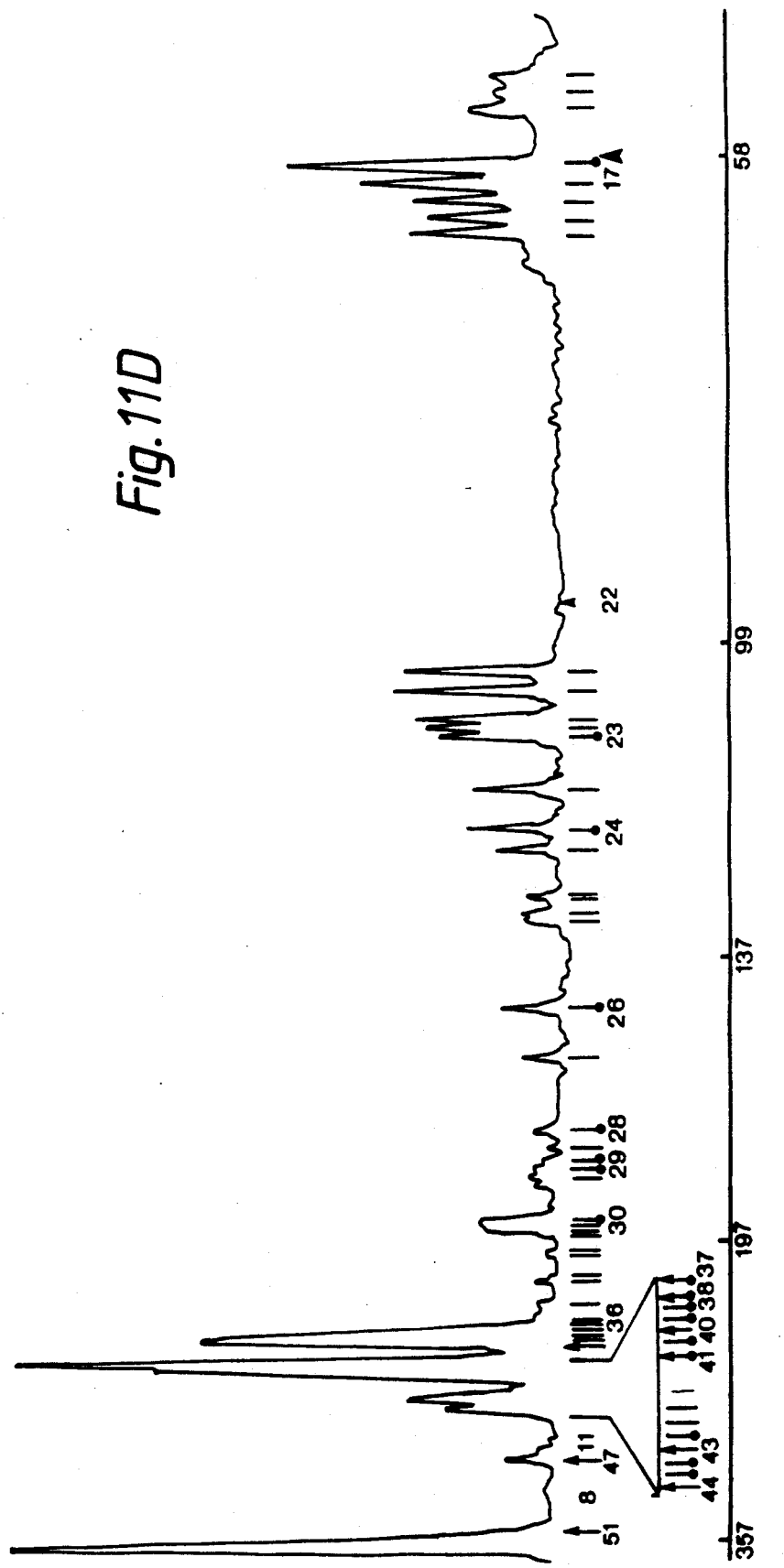

In the case of insertion/deletions the single C base deletion at A36 is readily detected by cleavage of the single looped-out C base in the antisense probe (FIG. 11d). The detectability of inserts in the unlabelled strand of the heteroduplex may be equivocal however. This is particularly possible as no mismatched or unmatched bases will be available for reaction. Thus one would either have to make probes from the gene which contain the insert or rely on T or C bases next to or near insertions to signal their presence. We have three situations in which to examine the latter possibility in neighbouring bases, the T base next to A19 in the 21 hydroxylase B sense probe, the C base next to A32 in the sense strand and the T base next to A34 in the antisense strand. In the case of A19, the T base has a very strong reactivity (FIG. 11a) but this may be due to it being an AT rich area. In the case of A32, the C base next to this is not reactive. However the T base three bases away is very reactive (FIG. 11a). In the case of A34 the T base next to the insert is very reactive (FIG. 11c). This is a small sample for generalisation but it is possible that under the conditions employed, inserts in the unlabelled DNA of the heteroduplex may only be detected by cleavage of the probe if there is a T base one or two bases from the insert. Thus it is predictable that an insert into a GC rich area may not be detectable with the limited cleavage used in these experiments. However it is possible that if such an insert was present as the only mutation in a long heteroduplex and if exhaustive reaction was carried out it might be detected.

The presence of a mismatch in a duplex allows study of its influence on the reactivity of nearby matched T and C bases. From a study of the data and its summary in Table 2, it can be seen that T and C bases 1 or 2 away from the mismatch are commonly reactive. Careful analysis of mismatches not involving T or C bases in the probe indicates that nearby T bases tend to be more reactive than nearby C bases in the same position. In fact eight out of 13 C bases next to mismatches were negative e.g. A23 antisense probe, A28 sense probe, A29 antisense (2 cases). Only one of 6 T bases next to mismatches was definitely negative. However, it is not possible to elucidate the reasons for this differential reactivity of C and T bases next to mismatches but it might be due to such factors as different ionic strength of the reaction mixture, difference in reagents, different reactivity of C and T bases, and different properties of AT and GC base pairs. Significance of reactivity of nearby bases can also be assessed by scoring the isolated single base pair mismatches which can be detected by an increased reactivity of matched T and C bases on the opposite strand when labelled. Ten of 19 such mismatches (excluding A17) can be detected under the reaction conditions.

The reactivity of a group of 3 or more contiguous T or C bases can be illustrated from the results. Not only is the unmatched C base at mutation A36 (antisense probe, FIG. 11d) reactive, but the 5 neighbouring C bases are also reactive. This phenomenon also occurs in the 4 C bases next to mismatch A30 (antisense probe, FIG. 11d). The reason for this is not clear except to suggest that when the first C base reacts the distortion makes the second more reactive and so on, i.e. a chain reaction A similar situation appears to occur in the case of T bases e.g. the three T bases each side of A18 (antisense probe, FIG. 11c) and also at A25 and A27 with the same probe (two AT pairs are reactive in each case). In these cases it is possible a different type of base pairing occurs.

Substantial transmission of a disturbance away from a mismatch or other phenomenon appears to occur in a few cases. For example two T bases 7 and 8 bases from the extra G base (A36, FIG. 11a) in the sense probe appear to have enhanced reactivity. Also the two T bases 4 and 5 bases from the A32-34 insertion (sense probe, FIG. 11a) appear to have enhanced reactivity. It is notable that a T base 2 away from the extra G base at A36 (antisense strand, FIG. 11a) does not show enhanced reactivity.

It had earlier been shown that osmium tetroxide reacts more slowly with C bases (Burton & Riley (15)). Mismatched C bases were reactive with osmium tetroxide at A35, A45 and A50 (sense probe) (FIGS. 10a and 11a).

There is little data to provide a strong indication of the distance that a single base pair mismatch can be from the end of a heteroduplex to allow detection by the chemicals i.e. its reactivity is greater than nearby matched bases. On the one hand, detection of A50 by a mismatched C base 38 base pairs from the end is easily possible (FIG. 10a). Detection at A51 by a mismatched C base in the antisense probe 9 bases from the end may be possible if assignation of the band to this mismatch is correct. However, another problem with the detection of this mismatch is that the band is just below the probe band (FIG. 10b, lane 7). On the other hand, the reactivity of matched T bases 6 and 8, and C bases 5 and 12 from the break in the unlabelled DNA at A17 indicate this may be close to the limit. Thus one could suggest on the current data the limit is between 6 and 9 bases by referring to the C bases but may be more than this for T bases. However, a mismatched T base at A18 (antisense probe) 25 bases from the A17 break is detectable by being more reactive than neighbouring bases on each side. This whole area may be reactive as 16 of these base pairs are AT. This presumably explains the reactivity of the lone matched T base between A17 and A18 (antisense strand, FIG. 11c).

Examination of tracks where the heteroduplexes have been exposed for two different times to the one reagent suggests that shorter incubation times allow better detection of mismatches in the larger fragments than in the shorter fragments and that the longer time reverses the situation. For example compare in FIG. 10b lane 5 and 6 and lane 9 and 10. In lane 10 the mismatch at A47 is not visible at this longer time but it is clearer that the C next to the A30 mismatch is the most reactive of the group of 4 as expected. This is not obvious in lane 9. Likewise in FIG. 10a lanes 5 and 6, the bands above A17 have disappeared in lane 6 and reactivities have appeared lower down.

Little can be said of the relative reactivities of particular mismatch types as differences could be due to the different contexts they are in. For example the relatively low reactivity of the T/G mismatch A28 (FIG. 11c) could be because it is bounded on each side by the more stable GC base pairs. Also the relative reactivity of two bases distant on the gel cannot be compared by band intensity due to the phenomenon described above, i.e. longer reaction decreases mismatch band intensity at the top of the gels and increases band intensity at the bottom. It is encouraging that the T/T mismatch at A31 (FIG. 11c) is very reactive as the example chosen in Example 1 was not completely cleaved.

The strengths of the method of the invention thus appear to be (a) No extra cloning is required beyond that for cloning and sequencing the wild type (reference) DNA. (b) It is a cleavage method allowing easy assessment. (c) Being a chemical method it may be more reproducible than enzymatic methods. (d) Comparison with a Maxam and Gilbert sequencing ladder and limited cleavage of a heteroduplex allows rapid and ready identification of position and type of mismatch. (e) As no mismatches have yet been found which do not cleave it is possible that all mismatches may be detectable. Thus if a labelled probe contains a mismatched T or C in its heteroduplex it can be readily detected. However, a probe of the opposite sense will contain mismatched T or C, respectively, and the mismatch then will be detected. (f) The method is rapid simple and inexpensive.

The system described here is ideally suited to comparison of related pieces of DNA or RNA such as virus isolates so that one can obtain a "pattern of difference" or "finger print" of the difference between two isolates Not only can one see single base pair mismatches of T and C bases in the probe but also insertions of T and C bases in the probe. Matched T and C bases will also be reactive when they are near mismatches or insertions These different reactivities all add to the complexity of a DNA comparison making the "pattern of difference" more useful due to its higher information content.

REFERENCES

1. Shenk, T. E., Rhodes, C., Rigby, P. W. J. and Berg, P. (1975) Proc.Natl.Acad.Sci.USA 72 989-993.
2. Myers, R. M., Lumelsky, N., Lerman, L. S. and Maniatis, T. (1985) Nature 313 495-498.
3. Myers, R. M., Larin, Z. and Maniatis, T. (1985) Science 230 1242-1246.
4. Winter, E., Yamamoto, F., Almoguera, C., and Perucho, M. (1985) Proc.Natl.Acad.Sci.USA 82 7575-7579.
5. Novack, D. F., Casna, N. J., Fischer, S. G. J., and Ford, J. P., (1986) Proc.Natl.Acad.Sci.USA 83 586-590.
6. Rodrigues, N. R., Dunham, I., Yu, C. Y., Carroll, M. C., Porter, R. R., and Campbell, R. D. (1987) EMBO.J 6 1653-1661.
7. Cramer, F. (1971) Prog.Nucl. Acid Res. 11 391-421.
8. Maxam, A. M. and Gilbert, W. (1980) Methods Enzymol. 65 499-560.
9. Sanger, F., Nicklen, S. and Coulson, A. R. (1977) Proc.Natl.Acad.Sci.USA 74 5463-5467.
10. Furlong, J. C., and Lilley, D. M. J. (1986) Nucl. Acid Res. 14 3995-4007.
11. Johnston, B. H. and Rich, A. (1985) Cell 42 713-724.
12. Kochetkov, N. K. and Budovskii, E. I. (1972) Organic Chemistry of Nucleic Acids, Part B. Plenum, London and New York.
13. Morozova, T. M. and Salganik, R. I. (1964) Biokhimiya 29, 17.
14. Rubin, C. M. and Schmid, C. W. (1980) Nucl. Acid Res. 8 4613-4619.
15. Burton, K. and Riley, W. T. (1966) Biochem.J. 98 70-77.
16. Lilley, D. M. J. and Palecek, E. (1984) EMBO J. 3, 1187-1192.
17. Cashmore, A. R., Brown, D. M. and Smith, J. D. (1972) J.Mol.Biol. 59, 359-373.
18. Mackow, E., Makino, Y., Shao, B., Zhang, Y-M., Markoff, L., Buckler-White, A., Guiler, M., Chanock, R. and Lai, C-J. (1987) Virology 159, 217-228.
19. Hahn, Y. S., Galler, R., Hunkapiller, T., Dalrymple, J. M., Strauss, J. H. and Strauss, E. G. (1988) Virology 162, 167-180.
20. Deubel, V., Kinney, R. M. and Trent, D. W. (1988) Virology 165, 234-244.
21. Sabin, A. B. and Schlesinger, R. W. (1945) Science 101, 640-642.
22. Morens, D. M., Larsen, L. K. and Halstead, S. B. (1987) J. Med. Virol. 22, 163-167.
23. Gruenberg, A., Woo, W. S., Biedrzycka, A. and Wright, P. J. (1988) J. Gen. Virol. 69, 1391-1398.
24. Biedrzycka, A., Cauchi, M., Bartholomeusz, A., Gorman, J. J. and Wright, P. J. (1987) J. Gen, Virol. 68, 1317-1326.
25. Khan, A. M. and Wright, P. J. (1987) J. Virol. Methods. 15, 121-130.
26. Cotton, R. G. H., Rodrigues, N. R. and Campbell, R. D. (1988) Proc. Natl. Acad. Sci. USA 85, 4397-4401.
27. Tinoco, Jnr, I., Borer, P. N., Dengler, B., Levine, M. D., Uhlenbeck, O. C., Crothers, D. M., and Gralla, J. (1972) Nature 246, 40-41.

TABLE 1

Summary of C and T mismatches cleaved

| MISMATCH* | MUTATION | PROBE | CLEAVAGE$ | SEQUENCES AROUND MISMATCH** |
|---|---|---|---|---|
| C/A | B3 | 5'/III/M | +ve(+ve) | TGCAC(C)TGCTG |
| C/T | B4 |  | 88(57) | CTCCC(C)ATCTA |
| C/C | B8 | 3'/VII/B | 93(79) | CCATG(C)TCGGC |
| C/A | B11 | 5'/VIII/B | 74(+ve) | CTCGG(C)AGTCA |
| C/C | B5 | 5'/IV/B | 90 | CCCCA(C)CTCCT |
| C/A | A13 | 5'/II/B | +ve | CGTCT(C)GCCAT |
| C/A | A14 |  | +ve | CCTCC(C)GCCTC |
| C/A | B1 | 3'/I/M | 84(81) | CCTCC(C)TTCAC |
| C/A | A82a++ | 5'/IX/A | 87 | GCTCC(C)GTACG |
| C/A | A24 | 5'/VI/B | E | CTATG(C)TGCCC |
| C/T | A35 | " | E | AGGTC(C)CTGGA |
| C/T | A45 | " | E | GAGGC(C)GAAGA |
| C/C | A48 | " | E(R) | GCCTT(C)ATCAG |
| C/C | A50 | " | E(R) | CCCCA(C)CTCCT |
| C/T | A43 | 3'/X/B | E(R) | CCAAC(C)CCTGC |
| C/A | A44 | " | E(R) | CCTCC(C)CAACC |
| C/T | A47 | " | E(R) | GAAGG(C)AGCTG |

TABLE 1-continued

Summary of C and T mismatches cleaved

| MISMATCH* | MUTATION$ | PROBE | CLEAVAGE$ | SEQUENCES AROUND MISMATCH** |
|---|---|---|---|---|
| C/T | A23 | 3'/XI/A | E(R) | CAAGA(C)CCCAT |
| C/A | A25 | " | E(R) | GAATT(C)AAGAC |
| C/A | A26 | " | E(R) | GAGAC(C)AGGAA |
| C/A | A27 | " | E(R) | GATCA(C)TTGAG |
| C/A | A28 | " | E | GAGGC(C)GAGGT |
| C/T | A29 | " | E | GGCTC(C)CACTT |
| T/T | A64 | 5'/XII/B | 17 | CATCA(T)CTGTT |
| T/C | B4 | 3'/III/B | 78 | TAGAT(T)GGGAG |
| T/G | B3 | 5'/III/B | 61 | TGCAC(T)TGCTG |
| T/G | B10a++ | 5'/VIII/B | 46 | GCTCC(T)GTACG |
| C/A | B11 | | (+ve) | CTCGG(C)AGTCA |
| T/C | A65 | 3'/XIII/A | 57 | AAGGA(T)GGAGT |
| C/C | A67 | | (+ve) | TTGAC(C)TCCTG |
| T/G | A30 | 5'/VI/B | E(R) | ACCTT(T)GGGGC |
| T/C | A29 | " | E(R) | AAGTG(T)GAGCC |
| T/C | A23 | " | E | ATGGG(T)TCTTG |
| T/G | A17 | " | E | AGGGC(T)GGGGG |
| T/T | A31 | 3'/X/B | E | GGGGA(T)GCCCC |
| T/G | A46 | " | E | GCAGC(T)GAGGG |
| T/G | A88 | 5'/XIV/B | E | TTAAT(T)CTGAG |
| T/G | A84 | " | E | TGCTC(T)TCCCG |
| C/A | A89 | " | (E) | GCTGG(C)CCTTT |

TABLE 2

Analysis of the reactivity of T and C bases at or near the differences created in the heteroduplex$^a$

| A mutation+ | Positive Probe | | | Negative Probe | | |
|---|---|---|---|---|---|---|
| | Mismatch | OSO$_4$ | Hyd. | Mismatch | OSO$_4$ | Hyd. |
| 17* | T/G | ++ | N(C1,C6,C10) | A/C | N(TGT7) | N(C1,C2) |
| 18* | A/G | N | N | T/C | ++(T1-3) | N |
| 19 | —/A | N(T1+++) | N | —/T | N | N |
| 20 | —/C | N | N | —/G | N | N |
| 21 | —/A | N | N | —/T | N | N |
| 22 | A/A | N | N | T/T | ++++(T1,T3,T5) | N(C2,C3) |
| 23* | T/C | +++ | N | A/G | N | N |
| 24* | C/A | N(T1) | ++++ | G/T | N(T3) | N |
| 25* | A/C | N(T1) | N | T/G | ++(T1,T2) | N |
| 26* | A/C | N(T1) | N | T/G | ++ | N(C1) |
| 27* | A/C | N(T1) | N | T/G | ++(T1,T2) | N |
| 28* | A/C | N | N | T/G | + | N |
| 29* | T/C | ++++ | N | A/G | N | N |
| 30* | T/G | +++(?T1,T2) | N | A/C | N | N(C1-C4) |
| 31* | A/A | N(T1++) | N(C1) | T/T | ++ | N |
| 32 | —/A | N(T3+++) | N | —/T | N(T4,T5) | N |
| 33 | —/G | N | N | —/C | N | N |
| 34 | —/G | N | N | —/C | N(T1,+++) | N |
| 35* | C/T | +(T2,T2) | +++(C1) | G/A | N | N |
| 36* | G/— | N(T7,T8) | N(C1) | C/— | N(Not T2) | ++++(C1-5) |
| 37 | G/A | N(T1) | N(C2) | C/T | N | |
| 38 | G/G | N | N | C/C | N | |
| 39 | T/T | ++++ | N | A/A | N | ++++ |
| 40 | G/T | N | N | C/A | N | |
| 41 | G/T | N | N | C/A | N(?T1) | |
| 42 | A/C | N | N | T/G | ++++(?T1,T2) | |
| 43* | G/A | N(T2) | N | C/T | N | ++(?C1,C2) |
| 44* | G/T | N(T2) | N | C/A | N | ++(?C1,C2) |
| 45* | C/T | ++ | ++++(C1) | G/A | N | N |
| 46* | A/C | N | N(C1,C2) | T/G | + | N |
| 47* | G/A | N | N(C1,C2) | C/T | N | ++ |
| 48 | C/C | N(T1,+++) | ++++ | G/G | N | |
| 49 | A/C | N(T1,+++T2) | N(C2) | T/G | + | N |
| 50* | C/C | +(T2) | ++++(C1) | G/G | N | N |
| 51* | G/T | N(T2,T4) | N | C/A | N | + |

We claim:

1. A method for detecting point mutations in a nucleic acid which comprises hybridizing a piece of control DNA or RNA that contains no mutations with a piece of test DNA or RNA that contains mutations to produce a linear heteroduplex; treating said linear heteroduplex with a solution containing an effective amount of aqueous hydroxylamine, or a solution containing an effective amount of aqueous osmium tetroxide and then with piperidine thereby causing cleavage at mismatched thymine or cytosine, subjecting the cleaved DNA or RNA to a separation treatment.

2. A method according to claim 1, wherein said heteroduplex is incubated with from 2 to 2.5M hydroxylamine hydrochloride for up to 2 hours at 37° C. at pH6.

3. A method according to claim 1, wherein said heteroduplex is incubated with 2.4% w/v osmium tetroxide for up to 1 hour at 37° C. at pH 7.7.

4. A method according to claim 1, wherein separation is by electrophoresis.

5. A method according to claim 1, wherein either strand of said control or test DNA or RNA is end-labelled or internally labelled.

6. A method according to claim 5, wherein only one strand in the heteroduplex is labelled, enabling indirect detection of mutations.

7. A method according to claim 5, wherein said label is a radioactive label, a fluorescent label or an enzyme label.

8. A method according to claim 1, wherein said treatment with hydroxylamine or osmium tetroxide is carried out on separate samples of said heteroduplex.

9. A method according to claim 1, wherein said test nucleic acid is RNA which is reacted to produce complementary test DNA and then said complementary test DNA is hybridized with complementary control DNA to produce said heteroduplex.

10. A method for detecting all point mutations in a nucleic acid which comprises: a) hybridizing a piece of labeled control DNA or RNA that contains no mutations with a piece of test DNA or RNA that contains mutations to produce a linear heteroduplex; b) hybridizing a piece complementary to said control DNA or RNA with a piece complementary to said test DNA or RNA; c) dividing each sample in two, one portion being treated with a solution containing an effective amount of aqueous osmium tetroxide and the other with a solution containing aqueous hydroxylamine then treating all four sample portions with piperidine, thereby causing cleavage at mismatched thymine or cytosine; d) subjecting the resulting material to a separation treatment; and e) detecting the fragments of cleaved DNA or RNA as indicative of point mutations.

11. A method according to claim 10, wherein said other portions of said samples are each incubated with from 2 to 2.5M hydroxylamine hydrochloride for up to 2 hours at 37° C. at pH6.

12. A method according to claim 10, wherein said one portions of said samples are each incubated with 2.4% w/v osmium tetroxide for up to 1 hour at 37° C. at pH 7.7.

13. A method according to claim 10, wherein said separation treatment is electrophoresis.

14. A method according to claim 10, wherein said control DNA or RNA complementary to said test DNA or RNA is end labelled or internally labelled.

15. A method according to claim 14, wherein said label is a radioactive label, a fluorescent label or enzyme label.

* * * * *

UNITED STATES PATENT AND TRADEMARK OFFICE
CERTIFICATE OF CORRECTION

PATENT NO. : 5,217,863
DATED : June 8, 1993
INVENTOR(S) : Richard G.H. Cotton, et. al.

It is certified that error appears in the above-indentified patent and that said Letters Patent is hereby corrected as shown below:

On the Title page, item [73], Assignee: should be -- The Murdoch Institute for Research Into Birth Defects Limited, an Australian corporation, Melbourne, Australia--.

Signed and Sealed this

First Day of November, 1994

*Attest:*

BRUCE LEHMAN

*Attesting Officer*   *Commissioner of Patents and Trademarks*